(12) United States Patent
Sung et al.

(10) Patent No.: US 9,394,570 B2
(45) Date of Patent: Jul. 19, 2016

(54) MARKER FOR COLON CANCER AND METHOD FOR DETECTING COLON CANCER

(75) Inventors: Jao Yiu Joseph Sung, Ma On Shan (HK); Jun Yu, Shatin (HK); Kin Fai Cheung, Shatin (HK)

(73) Assignee: The Chinese University of Hong Kong, Shatin, N.T., Hong Kong SAR (CN)

( * ) Notice: Subject to any disclaimer, the term of this patent is extended or adjusted under 35 U.S.C. 154(b) by 134 days.

(21) Appl. No.: 12/764,337

(22) Filed: Apr. 21, 2010

(65) Prior Publication Data

US 2011/0262910 A1    Oct. 27, 2011

(51) Int. Cl.
| C12Q 1/70 | (2006.01) |
| C07H 21/00 | (2006.01) |
| C12P 19/34 | (2006.01) |
| C12Q 1/68 | (2006.01) |

(52) U.S. Cl.
CPC ........ *C12Q 1/6886* (2013.01); *C12Q 2600/118* (2013.01); *C12Q 2600/154* (2013.01); *C12Q 2600/156* (2013.01)

(58) Field of Classification Search
CPC ........... C12Q 1/6886; C12Q 2600/156; C12Q 2600/118; C12Q 2600/154
See application file for complete search history.

(56) References Cited

U.S. PATENT DOCUMENTS

| 2002/0165382 A1 | 11/2002 | Basson | |
| 2003/0186235 A1 * | 10/2003 | Sun et al. | 435/6 |
| 2004/0249140 A1 | 12/2004 | Basson | |
| 2005/0287531 A1 * | 12/2005 | DeNise et al. | 435/6 |

FOREIGN PATENT DOCUMENTS

| WO | WO 0200927 A2 * | 1/2002 |
| WO | WO0200927 A2 * | 1/2002 |
| WO | WO 2009069984 A2 * | 6/2009 |

OTHER PUBLICATIONS

Ehrlich et al. (2002 Oncogene vol. 21 p. 5400).*
Cottrell (Clinical Biochemistry 2004 vol. 37 p. 595).*
Walsh et al teaches (Genes & Development (1999) vol. 13, pp. 26-36).*
Benner et al (Trends in Genetics (2001) vol. 17, pp. 414-418).*
Cheung et al (Nature Genetics, 2003, vol. 33, pp. 422-425).*
Skottman et al (Stem Cells (2006) vol. 24, pp. 151-167).*
Dermer et al. (Biotechnology vol. 12, Mar. 1994, p. 320).*
Ehrich (Proceedings National Academy of Sciences (2008) vol. 105, pp. 4844-4849).*
Ahuja et al (Cancer Research (1998) vol. 58, pp. 5489-5494).*
Hg-U133_PLUS_2:211886_S_AT(https://www.affymetrix.com/analysis/netaffx/fullrecord.affx?pk=HG-U133_PLUS_2:211886_S_AT, downloaded May 27, 2014).*
Cortese et al (Genomics (2008) vol. 91, pp. 492-502).*
Aerssens et al (Clinical Gastroenterology and Hepatology (2008) vol. 6, pp. 194-205).*
Cortese ( Dissertation (Bonn 2007, pp. 1-163).*
Bork et al ( Aging Cell (2010) vol. 9 pp. 54-63).*
Chapman et al (Developmental Dynamics (1996) vol. 206, pp. 379-390).*
NEB catalog(2000-2001 p. 34).*
Diffenbach (PCR methods and Applications (1993) vol. 3, pp. S30-S37).*
Roux et al(PCR Methods and Applications (1995) vol. 4, pp. s185-s194).*
Grunau et al ( Nucleic Acids Research (2001) vol. 29, e65).*
Ehrlich et al (Nucleic acids Research (1982) vol. 10, pp. 2709-2721).*
Meissner (Nature (2008) vol. 454, pp. 766-771).*
Cai, C.L. et al.; "T-box genes coordinate regional rates of proliferation and regional specification during cardiogenesis"; *Development* 2005;vol. 132, pp. 2475-2487.
Finotto, S.; "T-cell regulation in asthmatic diseases"; *Chem. Immunol. Allergy.* 2008, vol. 94, pp. 83-92.
Grady, W.M. et al.;"Genomic and epigenetic instability in colorectal cancer pathogenesis" *Gastroenterology*, 2008, vol. 135, pp. 1079-1099.
He, M.L. et al.; "Induction of apoptosis and inhibition of cell growth by developmental regulator hTBX5"; *Biochem Biophys Res Commun.* 2002, vol. 297, pp. 185-192.
Maitra, M. et al.; "Interaction of Gata4 and Gata6 with Tbx5 is critical for normal cardiac development" *Dev Biol.* 2009, vol. 326, pp. 368-377.
Mori, A.D. et al.; "Tbx5-dependent rheostatic control of cardiac gene expression and morphogenesis"; *Dev Biol.* 2006, vol. 297, pp. 566-586.
Nemer, M.; "Genetic insights into normal and abnormal heart development"; *Cardiovasc Pathol.* 2008, vol. 17, pp. 48-54.
Newbury-Ecob, R.A. et al., "Holt-Oram syndrome: a clinical genetic study" *J Med Genet* 1996, vol. 33, pp. 300-307.
Papaioannou, V.E. et al.; "The T-box gene family"; *Bioessays.* 1998, vol. 20, pp. 9-19.
Plageman, T.F. et al.; "Microarray analysis of Tbx5-induced genes expressed in the developing heart"; Dev Dyn. 2006, vol. 235, pp. 2868-2880.
Yu, J. et al.; "Methylation of protocadherin 10, a novel tumor suppressor, is associated with poor prognosis in patients with gastric cancer"; *Gastroenterology*, 2009, vol. 136, pp. 640-651.
Yu, J. et al.; "Promoter methylation of the Wnt/beta-catenin signaling antagonist Dkk-3 is associated with poor survival in gastric cancer"; *Cancer,* 2009, vol. 115, pp. 49-60.
Zitt, M. et al.; "DNA methylation in colorectal cancer—impact on screening and therapy monitoring modalities?"; *Dis Markers.* 2007, vol. 23, pp. 51-71.
Cai et al., "T-box genes coordinate regional rates of proliferation and regional specification during cardiogenesis," 2005, Development, 132, pp. 2475-2487.
Finotto et al., "T-Cell Regulation in Asthmatic Diseases," 2008, Chem. lmmunol. Allergy, vol. 94, pp. 88-92.
Grady et al., "Reviews in Basic and Clinical Gastroenterology: Genomic and Epigenetic Instability in Colorectal Cancer Pathogenesis," 2008, Gastroenterology, 135, 1079-1099.

(Continued)

*Primary Examiner* — Steven Pohnert
(74) *Attorney, Agent, or Firm* — Kilpatrick Townsend & Stockton LLP

(57) ABSTRACT

In embodiments the expression or methylation of the TBX5 gene is used as a marker for the presence and prognosis of colon cancer. In further embodiments methods for detecting colon cancer are disclosed as are methods for inhibiting the growth of colon cancer cells.

4 Claims, 4 Drawing Sheets

(56) References Cited

OTHER PUBLICATIONS

He et al., Induction of apoptosis and inhibition of cell growth by developmental regulator hTBX5, 2002, Biochemical and Biophysical Research Communications, 297, pp. 185-192.

Maitra et al., "Interaction of Gata4 and Gata6 with TbX5 is critical for normal cardiac development," 2009, Developmental Biology, 326, pp. 368-377.

Mod et al., "Tbx5-dependant rheostatic control of cardiac gene expression and morphogenesis," 2006, Developmental Biology, 297, pp. 566-586.

Nemer et al., "Genetic Insights into normal and abnormal heart development," 2008, Cardiovascular Pathology, 17, 48-54.

Newbury-Ecob et al., "Holt-Oram syndrome: a clinical genetic study," 1996, J. Med. Genet., 33, 300-307.

Papaioannou et al., "The T-Box gene family," 1998, BioEssays 20(1), pp. 9-10.

Plageman et al., "Microarray Analysis of Tbx5-Induced Genes Expressed in the Developing Heart," 2006, Developmental Dynamics, 235, pp. 2868-2880.

Yu et al., "Methylation of protocadherin 10, a novel tumor suppressor, is associated with poor prognosis in patients with gastric cancer," 2009, Gastroenterology, 136(2), 640-651.

Yu et al., "Promoter methylation of the Wnt/beta-catenin signaling antagonist Dkk-3 is associated with poor survival in gastric cancer," 2009, Cancer, 115(1), pp. 49-60.

Zitt et al., "DNA methylation in colorectal cancer—Impact on screening and therapy monitoring modalities?," 2007, Disease Markers, 23, pp. 51-71.

\* cited by examiner

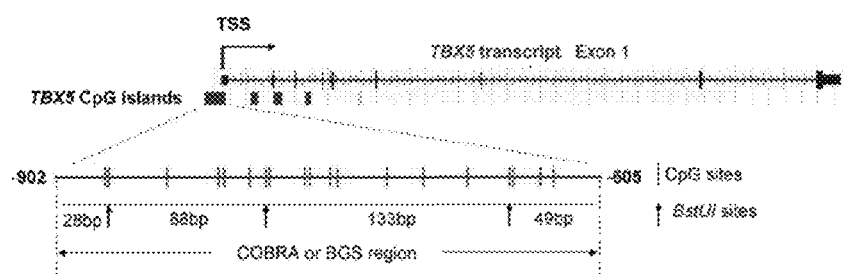
Fig. 1A
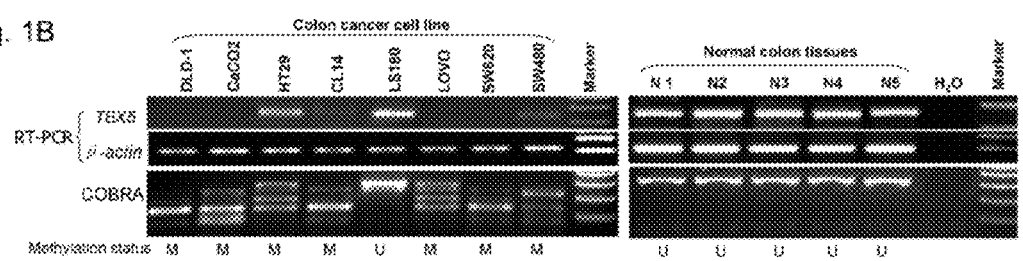
Fig. 1B
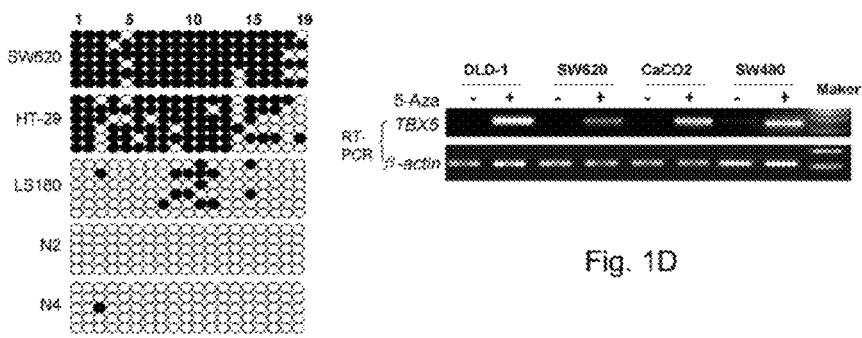
Fig. 1C
Fig. 1D

Fig. 2(A1)     Fig. 2(A2)     Fig. 2(A3)
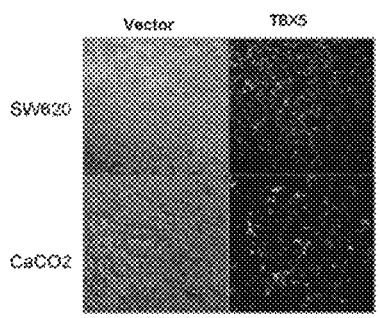 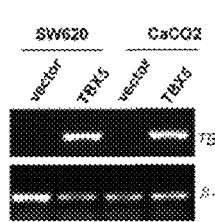 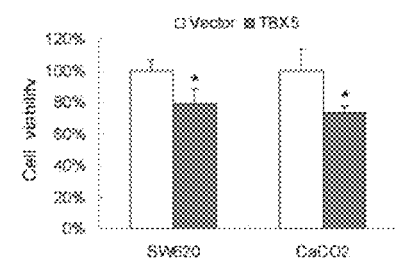
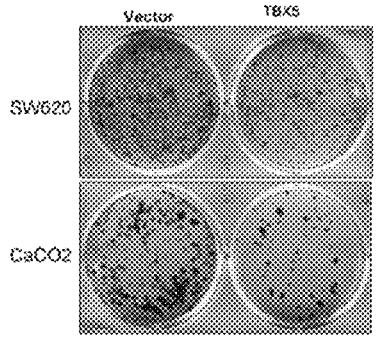 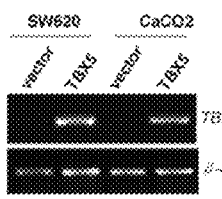 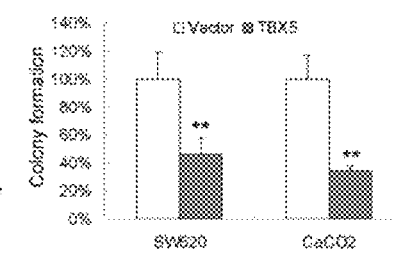
Fig. 2(B1)     Fig. 2(B2)     Fig. 2(B3)

Fig. 3(A1)
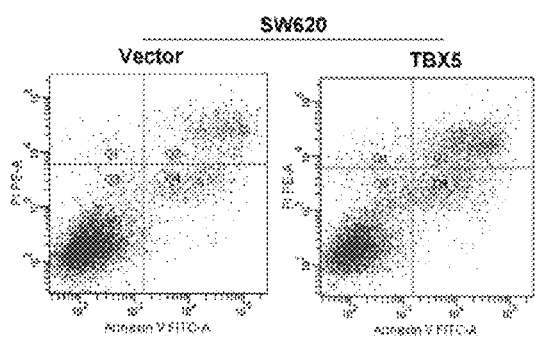
Fig. 3(A2)
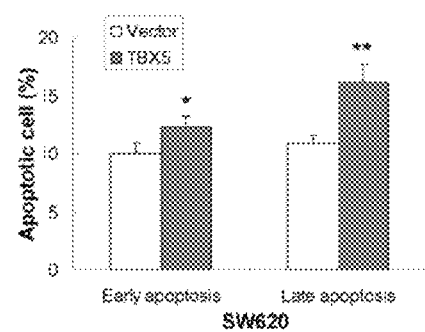
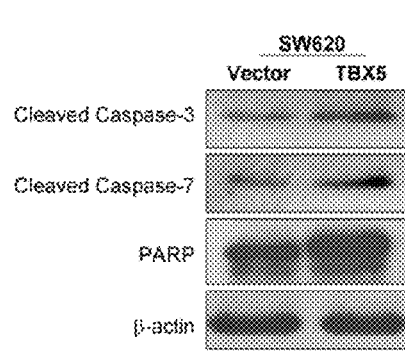
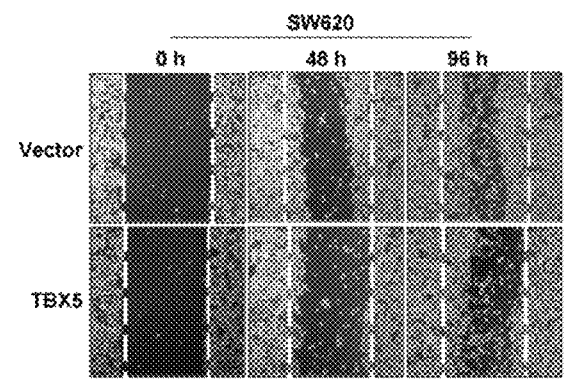
Fig. 3(A3)
Fig. 3(B)

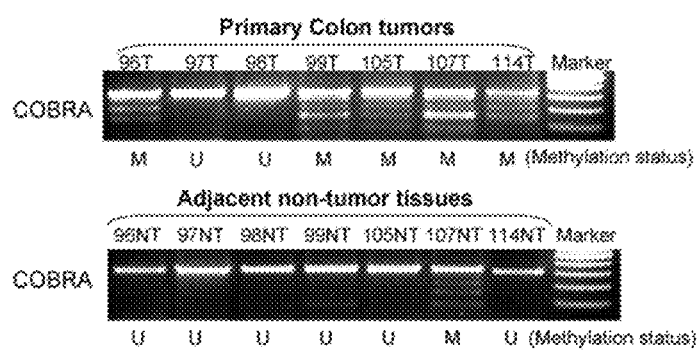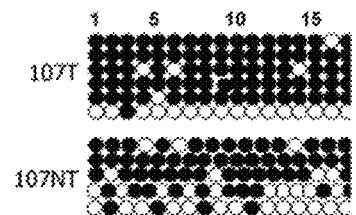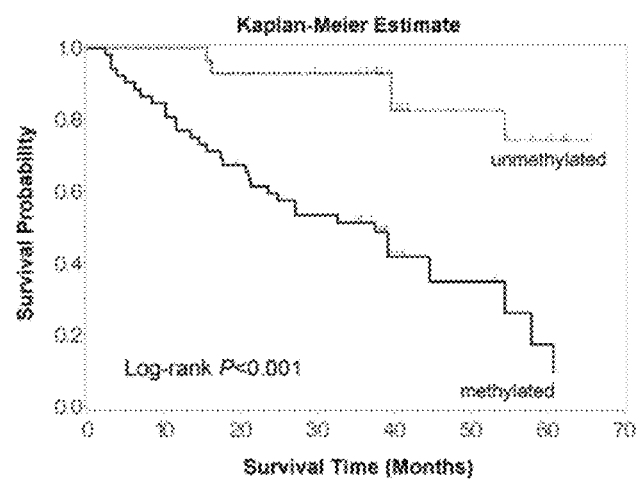

```
                               SEQUENCE LISTING

<160> NUMBER OF SEQ ID NOS: 27

<210> SEQ ID NO 1
<211> LENGTH: 298
<212> TYPE: DNA
<213> ORGANISM: Homo sapiens
<220> FEATURE:
<223> OTHER INFORMATION: promoter sequence of human TBX5 gene

<400> SEQUENCE: 1
cactgcagcc tggctgagag aaaggacgcg ggttgtgctc tctggaagca aagggtctg     60 cggcccagct ggcctgggag cttgtggccg gcgctggaag ctgcccgctc tccccgcggg   120
cctgaccttg gctcccgccg cagctctgcc ggccgactgc ctccctgcac attttgctgc   180
cgttccagtc cttacaggac cgggcctgga gccaggccat gcttcggaaa gccctggggg   240
ttggggacgc gcaaaaccca gaatcgaacc ccgaagctgg gggcaagtcc agattcag    298

<210> SEQ ID NO 2
<211> LENGTH: 20
<212> TYPE: DNA
<213> ORGANISM: Artificial Sequence
<220> FEATURE:
<223> OTHER INFORMATION: synthetic forward primer for human TBX5 mRNA

<400> SEQUENCE: 2
ctcaagctca ccaacaacca                                                20

<210> SEQ ID NO 3
<211> LENGTH: 20
<212> TYPE: DNA
<213> ORGANISM: Artificial Sequence
<220> FEATURE:
<223> OTHER INFORMATION: synthetic reverse primer for human TBX5 mRNA

<400> SEQUENCE: 3
caggaaagac gtgagtgcag                                                20

<210> SEQ ID NO 4
<211> LENGTH: 26
<212> TYPE: DNA
<213> ORGANISM: Artificial Sequence
<220> FEATURE:
<223> OTHER INFORMATION: synthetic forward primer for human TBX5
      promoter

<400> SEQUENCE: 4
tattgtagtt tggttgagag aaagga                                         26

<210> SEQ ID NO 5
<211> LENGTH: 26
<212> TYPE: DNA
<213> ORGANISM: Artificial Sequence
<220> FEATURE:
<223> OTHER INFORMATION: synthetic reverse primer for human TBX5
      promoter

<400> SEQUENCE: 5
ctaaatctaa acttaccccc aacttc                                         26

<210> SEQ ID NO 6
```

```
<211> LENGTH: 4
<212> TYPE: DNA
<213> ORGANISM: Artificial Sequence
<220> FEATURE:
<223> OTHER INFORMATION: synthetic BstUI cleavage sequence

<400> SEQUENCE: 6 cgcg                                                                       4

<210> SEQ ID NO 7
<211> LENGTH: 151
<212> TYPE: DNA
<213> ORGANISM: Artificial Sequence
<220> FEATURE:
<223> OTHER INFORMATION: synthetic amplified portion of human TBX5
      transcript variant no. 1

<400> SEQUENCE: 7
ctcaagctca ccaacaacca cctggaccca tttgggcata ttattctaaa ttccatgcac         60
aaataccagc ctagattaca catcgtgaaa gcggatgaaa ataatggatt tggctcaaaa        120
aatacagcgt tctgcactca cgtctttcct g                                       151

<210> SEQ ID NO 8
<211> LENGTH: 23
<212> TYPE: DNA
<213> ORGANISM: Artificial Sequence
<220> FEATURE:
<223> OTHER INFORMATION: synthetic sense primer for human TBX5 promoter

<400> SEQUENCE: 8 ggggttgtgtt ttttggaagt aaa                                                23

<210> SEQ ID NO 9
<211> LENGTH: 23
<212> TYPE: DNA
<213> ORGANISM: Artificial Sequence
<220> FEATURE:
<223> OTHER INFORMATION: synthetic sense primer for human TBX5 promoter

<400> SEQUENCE: 9
gtttagttgg tttgggagtt tgt                                                 23

<210> SEQ ID NO 10
<211> LENGTH: 26
<212> TYPE: DNA
<213> ORGANISM: Artificial Sequence
<220> FEATURE:
<223> OTHER INFORMATION: synthetic sense primer for human TBX5 promoter

<400> SEQUENCE: 10
gattgttttt ttgtatattt tgttgt                                              26

<210> SEQ ID NO 11
<211> LENGTH: 26
<212> TYPE: DNA
<213> ORGANISM: Artificial Sequence
<220> FEATURE:
<223> OTHER INFORMATION: synthetic antisense primer for human TBX5
      promoter

<400> SEQUENCE: 11
acaacaaaat atacaaaaaa acaatc                                              26

<210> SEQ ID NO 12
<211> LENGTH: 518
```

```
<212> TYPE: PRT
<213> ORGANISM: Homo sapiens
<220> FEATURE:
<223> OTHER INFORMATION: Human TBX5 amino acid sequence

<400> SEQUENCE: 12
```

| | | | | | | | | | | | | | | |
|---|---|---|---|---|---|---|---|---|---|---|---|---|---|---|
| Met | Ala | Asp | Ala | Asp | Glu | Gly | Phe | Gly | Leu | Ala | His | Thr | Pro | Leu | Glu |
| 1 | | | | 5 | | | | | 10 | | | | | 15 | |
| Pro | Asp | Ala | Lys | Asp | Leu | Pro | Cys | Asp | Ser | Lys | Pro | Glu | Ser | Ala | Leu |
| | | | 20 | | | | | 25 | | | | | 30 | | |
| Gly | Ala | Pro | Ser | Lys | Ser | Pro | Ser | Pro | Gln | Ala | Ala | Phe | Thr | Gln |
| | | | 35 | | | | | 40 | | | | | 45 | | |
| Gln | Gly | Met | Glu | Gly | Ile | Lys | Val | Phe | Leu | His | Glu | Arg | Glu | Leu | Trp |
| | | 50 | | | | | 55 | | | | | 60 | | | |
| Leu | Lys | Phe | His | Glu | Val | Gly | Thr | Glu | Met | Ile | Ile | Thr | Lys | Ala | Gly |
| 65 | | | | | 70 | | | | | 75 | | | | | 80 |
| Arg | Arg | Met | Phe | Pro | Ser | Tyr | Lys | Val | Lys | Val | Thr | Gly | Leu | Asn | Pro |
| | | | | 85 | | | | | 90 | | | | | 95 | |
| Lys | Thr | Lys | Tyr | Ile | Leu | Leu | Met | Asp | Ile | Val | Pro | Ala | Asp | Asp | His |
| | | | 100 | | | | | 105 | | | | | 110 | | |
| Arg | Tyr | Lys | Phe | Ala | Asp | Asn | Lys | Trp | Ser | Val | Thr | Gly | Lys | Ala | Glu |
| | | | 115 | | | | | 120 | | | | | 125 | | |
| Pro | Ala | Met | Pro | Gly | Arg | Leu | Tyr | Val | His | Pro | Asp | Ser | Pro | Ala | Thr |
| | | 130 | | | | | 135 | | | | | 140 | | | |
| Gly | Ala | His | Trp | Met | Arg | Gln | Leu | Val | Ser | Phe | Gln | Lys | Leu | Lys | Leu |
| 145 | | | | | 150 | | | | | 155 | | | | | 160 |
| Thr | Asn | Asn | His | Leu | Asp | Pro | Phe | Gly | His | Ile | Ile | Leu | Asn | Ser | Met |
| | | | | 165 | | | | | 170 | | | | | 175 | |
| His | Lys | Tyr | Gln | Pro | Arg | Leu | His | Ile | Val | Lys | Ala | Asp | Glu | Asn | Asn |
| | | | 180 | | | | | 185 | | | | | 190 | | |
| Gly | Phe | Gly | Ser | Lys | Asn | Thr | Ala | Phe | Cys | Thr | His | Val | Phe | Pro | Glu |
| | | | 195 | | | | | 200 | | | | | 205 | | |
| Thr | Ala | Phe | Ile | Ala | Val | Thr | Ser | Tyr | Gln | Asn | His | Lys | Ile | Thr | Gln |
| | | 210 | | | | | 215 | | | | | 220 | | | |
| Leu | Lys | Ile | Glu | Asn | Asn | Pro | Phe | Ala | Lys | Gly | Phe | Arg | Gly | Ser | Asp |
| 225 | | | | | 230 | | | | | 235 | | | | | 240 |
| Asp | Met | Glu | Leu | His | Arg | Met | Ser | Arg | Met | Gln | Ser | Lys | Glu | Tyr | Pro |
| | | | | 245 | | | | | 250 | | | | | 255 | |
| Val | Val | Pro | Arg | Ser | Thr | Val | Arg | Gln | Lys | Val | Ala | Ser | Asn | His | Ser |
| | | | 260 | | | | | 265 | | | | | 270 | | |
| Pro | Phe | Ser | Ser | Glu | Ser | Arg | Ala | Leu | Ser | Thr | Ser | Ser | Asn | Leu | Gly |
| | | | 275 | | | | | 280 | | | | | 285 | | |
| Ser | Gln | Tyr | Gln | Cys | Glu | Asn | Gly | Val | Ser | Gly | Pro | Ser | Gln | Asp | Leu |
| | | 290 | | | | | 295 | | | | | 300 | | | |
| Leu | Pro | Pro | Pro | Asn | Pro | Tyr | Pro | Leu | Pro | Gln | Glu | His | Ser | Gln | Ile |
| 305 | | | | | 310 | | | | | 315 | | | | | 320 |
| Tyr | His | Cys | Thr | Lys | Arg | Lys | Glu | Glu | Glu | Cys | Ser | Thr | Thr | Asp | His |
| | | | | 325 | | | | | 330 | | | | | 335 | |
| Pro | Tyr | Lys | Lys | Pro | Tyr | Met | Glu | Thr | Ser | Pro | Ser | Glu | Glu | Asp | Ser |
| | | | 340 | | | | | 345 | | | | | 350 | | |
| Phe | Tyr | Arg | Ser | Ser | Tyr | Pro | Gln | Gln | Gln | Gly | Leu | Gly | Ala | Ser | Tyr |
| | | | 355 | | | | | 360 | | | | | 365 | | |
| Arg | Thr | Glu | Ser | Ala | Gln | Arg | Gln | Ala | Cys | Met | Tyr | Ala | Ser | Ser | Ala |
| | | | 370 | | | | | 375 | | | | | 380 | | |

```
Pro Pro Ser Glu Pro Val Pro Ser Leu Glu Asp Ile Ser Cys Asn Thr
385                 390                 395                 400

Trp Pro Ser Met Pro Ser Tyr Ser Ser Cys Thr Val Thr Thr Val Gln
            405                 410                 415

Pro Met Asp Arg Leu Pro Tyr Gln His Phe Ser Ala His Phe Thr Ser
        420                 425                 430

Gly Pro Leu Val Pro Arg Leu Ala Gly Met Ala Asn His Gly Ser Pro
        435                 440                 445

Gln Leu Gly Glu Gly Met Phe Gln His Gln Thr Ser Val Ala His Gln
    450                 455                 460

Pro Val Val Arg Gln Cys Gly Pro Gln Thr Gly Leu Gln Ser Pro Gly
465                 470                 475                 480

Thr Leu Gln Pro Pro Glu Phe Leu Tyr Ser His Gly Val Pro Arg Thr
            485                 490                 495

Leu Ser Pro His Gln Tyr His Ser Val His Gly Val Gly Met Val Pro
            500                 505                 510

Glu Trp Ser Asp Asn Ser
        515

<210> SEQ ID NO 13
<211> LENGTH: 3921
<212> TYPE: DNA
<213> ORGANISM: Homo sapiens
<220> FEATURE:
<223> OTHER INFORMATION: mRNA sequence of human TBX5 transcript variant
      1

<400> SEQUENCE: 13
catgccttat gcaagagacc tcagtccccc ggaacaactc gatttccttc caatagaggt      60
ctgaggtgga ctcccacctc ccttcgtgaa gagttccctc ctctccccct tcctaagaaa     120
gtcgatcttg gctctatttg tgtcttatgt tcatcaccct cattcctccg gagaaagccg     180
ggttggttta tgtctttatt tattcccggg gccaagacgt ccggaacctg tggctgcgca     240
gacccggcac tgataggcga agacggagag aaatttacct cccgccgctg cccccagcc     300 aaacgtgaca gcgcgcgggc cggttgcgtg actcgtgacg tctccaagtc ctataggtgc     360
agcggctggt gagatagtcg ctatcgcctg gttgcctctt tattttactg gggtatgcct     420
ggtaataaac agtaatattt aatttgtcgg agaccacaaa ccaaccttga gctgggaggt     480
acgtgctctt cttgacagac gttggaagaa gacctggcct aaagaggtct cttttggtgg     540 tcctttcaa agtcttcacc tgagccctgc tctccagcga ggcgcactcc tggcttttgc     600
gctccaaaga agaggtggga tagttggaga gcagaacctt gcgcgggcac agggccctgg     660
gcgcaccatg gccgacgcag acgagggctt tggcctggcg cacacgcctc tggagcctga     720
cgcaaaagac ctgccctgcg attcgaaacc cgagagcgcg ctcggggccc ccagcaagtc     780
cccgtcgtcc ccgcaggccg ccttcaccca gcagggcatg gagggaatca agtgtttct     840 ccatgaaaga gaactgtggc taaaattcca cgaagtgggc acggaaatga tcataaccaa     900
ggctggaagg cggatgtttc ccagttacaa agtgaaggtg acgggcctta atcccaaaac     960
gaagtacatt cttctcatgg acattgtacc tgccgacgat cacagataca aattcgcaga    1020
taataaatgg tctgtgacgg gcaaagctga gcccgccatg cctggccgcc tgtacgtgca    1080
cccagactcc cccgccaccg gggcgcattg gatgaggcag ctcgtctcct tccagaaact    1140
caagctcacc aacaaccacc tggacccatt tgggcatatt attctaaatt ccatgcacaa    1200
ataccagcct agattacaca tcgtgaaagc ggatgaaaat aatggatttg gctcaaaaaa    1260
```

```
tacagcgttc tgcactcacg tctttcctga gactgcgttt atagcagtga cttcctacca    1320
gaaccacaag atcacgcaat taaagattga gaataatccc tttgccaaag gatttcgggg    1380
cagtgatgac atggagctgc acagaatgtc aagaatgcaa agtaaagaat atcccgtggt    1440
ccccaggagc accgtgaggc aaaaagtggc ctccaaccac agtcctttca gcagcgagtc    1500
tcgagctctc tccacctcat ccaatttggg gtcccaatac cagtgtgaga atggtgtttc    1560
cggcccctcc caggacctcc tgcctccacc caacccatac ccactgcccc aggagcatag    1620
ccaaatttac cattgtacca agaggaaaga ggaagaatgt tccaccacag accatcccta    1680
taagaagccc tacatggaga catcacccag tgaagaagat tccttctacc gctctagcta    1740
tccacagcag cagggcctgg gtgcctccta caggacagag tcggcacagc ggcaagcttg    1800
catgtatgcc agctctgcgc ccccagcga gcctgtgccc agcctagagg acatcagctg    1860
caacacgtgg ccaagcatgc cttcctacag cagctgcacc gtcaccaccg tgcagcccat    1920
ggacaggcta ccctaccagc acttctccgc tcacttcacc tcggggcccc tggtccctcg    1980
gctggctggc atggccaacc atggctcccc acagctggga gagggaatgt tccagcacca    2040
gacctccgtg gcccaccagc ctgtggtcag gcagtgtggg cctcagactg gcctgcagtc    2100
ccctggcacc cttcagcccc ctgagttcct ctactctcat ggcgtgccaa ggactctatc    2160
ccctcatcag taccactctg tgcacggagt tggcatggtg ccagagtgga gcgacaatag    2220
ctaaagtgag gcctgcttca caacagacat ttcctagaga aagagagaga gagaggagaa    2280
agagagagaa ggagagagac agtagccaag agaaccccac ggacaagatt tttcatttca    2340
cccaatgttc acatctgcac tcaaggtcgc tggatgctga tctaatcagt agcttgaaac    2400 cacaattta aaaatgtgac tttcttgttt tgtctcaaaa cttaaaaaaa caaacacaaa    2460
aagatgagtc ccaccccca ctaccaccac acccatcaac cagccacatt cacgctactc    2520
cccagatctc ttccccatt ccttcttttg ggctctagaa agtcttgcct cattgagtgt    2580
ttttccctag tgcgtagttg gagtctgtcc ctgtcttggt gttaatgttg acattgttat    2640
ataataaatg ataatatatt ttttctttc aattttctta atgggaccca gtcccttatt    2700 tgggggagg tctgaggcaa gtatattca aaatatgtac ttgcgggatt cccttcaagt    2760
aaaccatccc tgaaacctaa attcacgttt ccccttgact aagaaaagca cctacctctg    2820
ccatgtgatg tttctgaaaa gcctctgtat gtccccattt gctttggttt tgtcctgcct    2880
tctccaatat cacgtgctca gttttgcctc tacttaccca tggagtcagg ataacactga    2940
cgctccctgg catcctatct tattcagccc taccatcttg ccagtctgt ctttccagct    3000 gtctgtcgct aaaacgtggc ctatagcttc ccttccggaa agcttgcttt gaaaaactta    3060
aaaagccccc gtttacatgt aggcaggact gtgataacag tgcaagctct gtgttgacaa    3120
gagttgtgga caaaaagcca aaataaatat tcttcctgat taaaaaaatt ttttttgaaa    3180
aaaacaaggc cagccccaac cttccaaacc tccatcacca acaacccaaa ctggatgtca    3240
agcaaaatgc acaattccta cagaagaggc aagacacagt caccaatgat atctcgccaa    3300
agaaaccacg cccacaccaa tgccaacaca aaactgtgtt tactgaaagc cgaaaacagt    3360
attaaaaaaa gtgtgtaagt aaagtgttat ggtagggttc ttcagatgta atatttact    3420 ggtactattt atttataaat aggaattcta attaagtaat aacatgaaat gaaacccagc    3480
ataggagctg gccaagagct tttaatttta ttgatactca aaaccaagtt tgtgtttttt    3540 tgttttttt tgttttttc ctctttcgaa tgtgctttgc ttttttgat taaaagaat    3600
```

-continued

```
tttttttttc ctttttttata aacagaccct aataaagaga acagggtaag atgtgaggct    3660
gagtgtgttt aagtacgtga gagagtgtga gtgtgtttgt aagtgagtgt ccctatgcga    3720
ttatgtctct ttacgttgct aaggggggag ggtgaggatt aagtactcgt gccttatatt    3780
tgtgtgccaa ttaatgccta ataaatacca tgtgcttaaa caagtaaaaa aaaaaaaaaa    3840
aaaaaaaaaa aaaaaaaaaa aaaaaaaaaa aaaaaaaaaa aaaaaaaaaa aaaaaaaaaa    3900
aaaaaaaaaa aaaaaaaaa a                                               3921

<210> SEQ ID NO 14
<211> LENGTH: 20
<212> TYPE: DNA
<213> ORGANISM: Artificial Sequence
<220> FEATURE:
<223> OTHER INFORMATION: synthetic primer pair (i) sense primer for
      human TBX5 mRNA

<400> SEQUENCE: 14
taggcgaaga cggagagaaa                                                 20

<210> SEQ ID NO 15
<211> LENGTH: 20
<212> TYPE: DNA
<213> ORGANISM: Artificial Sequence
<220> FEATURE:
<223> OTHER INFORMATION: synthetic primer pair (i) anti-sense primer for
      human TBX5 mRNA

<400> SEQUENCE: 15
gctcaaggtt ggtttgtggt                                                 20

<210> SEQ ID NO 16
<211> LENGTH: 20
<212> TYPE: DNA
<213> ORGANISM: Artificial Sequence
<220> FEATURE:
<223> OTHER INFORMATION: synthetic primer pair (ii) sense primer for
      human TBX5 mRNA

<400> SEQUENCE: 16
accacaaacc aaccttgagc                                                 20

<210> SEQ ID NO 17
<211> LENGTH: 20
<212> TYPE: DNA
<213> ORGANISM: Artificial Sequence
<220> FEATURE:
<223> OTHER INFORMATION: synthetic primer pair (ii) anti-sense primer
      for human TBX5 mRNA

<400> SEQUENCE: 17
gcaaggttct gctctccaac                                                 20

<210> SEQ ID NO 18
<211> LENGTH: 20
<212> TYPE: DNA
<213> ORGANISM: Artificial Sequence
<220> FEATURE:
<223> OTHER INFORMATION: synthetic primer pair (iii) sense primer for
      human TBX5 mRNA

<400> SEQUENCE: 18
tcataaccaa ggctggaagg                                                 20

<210> SEQ ID NO 19
```

```
<211> LENGTH: 20
<212> TYPE: DNA
<213> ORGANISM: Artificial Sequence
<220> FEATURE:
<223> OTHER INFORMATION: synthetic primer pair (iii) anti-sense primer
      for human TBX5 mRNA

<400> SEQUENCE: 19
gcccgtcaca gaccatttat                                               20

<210> SEQ ID NO 20
<211> LENGTH: 20
<212> TYPE: DNA
<213> ORGANISM: Artificial Sequence
<220> FEATURE:
<223> OTHER INFORMATION: synthetic primer pair (iv) sense primer for
      human TBX5 mRNA

<400> SEQUENCE: 20
agctctctcc acctcatcca                                               20

<210> SEQ ID NO 21
<211> LENGTH: 20
<212> TYPE: DNA
<213> ORGANISM: Artificial Sequence
<220> FEATURE:
<223> OTHER INFORMATION: synthetic primer pair (iv) anti-sense primer
      for human TBX5 mRNA

<400> SEQUENCE: 21
ttcactgggt gatgtctcca                                               20

<210> SEQ ID NO 22
<211> LENGTH: 20
<212> TYPE: DNA
<213> ORGANISM: Artificial Sequence
<220> FEATURE:
<223> OTHER INFORMATION: synthetic primer pair (v) sense primer for
      human TBX5 mRNA

<400> SEQUENCE: 22
catcaaccag ccacattcac                                               20

<210> SEQ ID NO 23
<211> LENGTH: 20
<212> TYPE: DNA
<213> ORGANISM: Artificial Sequence
<220> FEATURE:
<223> OTHER INFORMATION: synthetic primer pair (v) anti-sense primer for
      human TBX5

<400> SEQUENCE: 23
agggactggg tcccattaag                                               20

<210> SEQ ID NO 24
<211> LENGTH: 20
<212> TYPE: DNA
<213> ORGANISM: Artificial Sequence
<220> FEATURE:
<223> OTHER INFORMATION: synthetic primer pair (vi) sense primer for
      human TBX5

<400> SEQUENCE: 24
tttggttttg tcctgccttc                                               20

<210> SEQ ID NO 25
<211> LENGTH: 20
```

```
<212> TYPE: DNA
<213> ORGANISM: Artificial Sequence
<220> FEATURE:
<223> OTHER INFORMATION: synthetic primer pair (vi) anti-sense primer
      for human TBX5

<400> SEQUENCE: 25
ccacgtttta gcgacagaca                                              20

<210> SEQ ID NO 26
<211> LENGTH: 20
<212> TYPE: DNA
<213> ORGANISM: Artificial Sequence
<220> FEATURE:
<223> OTHER INFORMATION: synthetic primer pair (vii) sense primer for
      human TBX5

<400> SEQUENCE: 26
ccaatgccaa cacaaaactg                                              20

<210> SEQ ID NO 27
<211> LENGTH: 20
<212> TYPE: DNA
<213> ORGANISM: Artificial Sequence
<220> FEATURE:
<223> OTHER INFORMATION: synthetic primer pair (vii) anti-sense primer
      for human TBX5

<400> SEQUENCE: 27
agctcctatg ctgggtttca                                              20
```

MARKER FOR COLON CANCER AND METHOD FOR DETECTING COLON CANCER

FIELD

The subject matter disclosed generally relates to markers for colon cancer, and methods for detecting colon cancer.

REFERENCE TO A "SEQUENCE LISTING," A TABLE, OR A COMPUTER PROGRAM LISTING APPENDIX SUBMITTED AS AN ASCII TEXT FILE

The Sequence Listing written in file SEQTXT 087509-001300US.TXT, created on Apr. 20, 2010, 16,384 bytes, machine format IBM-PC, MS-Windows operating system, is hereby incorporated by reference in its entirety for all purposes.

BACKGROUND

The following prior art publications are noted:
1. Grady W M, Carethers J M. Genomic and epigenetic instability in colorectal cancer pathogenesis. Gastroenterology. 2008; 135:1079-99.
2. Zitt M, Zitt M, Müller H M. DNA methylation in colorectal cancer—impact on screening and therapy monitoring modalities? Dis Markers. 2007; 23:51-71.
3. Plageman T F Jr, Yutzey K E. Microarray analysis of Tbx5-induced genes expressed in the developing heart. Dev Dyn. 2006; 235:2868-80.
4. Mori A D, Zhu Y, Vahora I, Nieman B, Koshiba-Takeuchi K, Davidson L, Pizard A, Seidman J G, Seidman C E, Chen X J, Henkelman R M, Bruneau B G. Tbx5-dependent rheostatic control of cardiac gene expression and morphogenesis. Dev Biol. 2006; 297:566-86.
5. Maitra M, Schluterman M K, Nichols H A, Richardson J A, Lo C W, Srivastava D, Garg V. Interaction of Gata4 and Gata6 with Tbx5 is critical for normal cardiac development. Dev Biol. 2009; 326:368-77.
6. He M L, Chen Y, Peng Y, Jin D, Du D, Wu J, Lu P, Lin M C, Kung H F. Induction of apoptosis and inhibition of cell growth by developmental regulator hTBX5. Biochem Biophys Res Commun. 2002; 297:185-92.
7. Newbury-Ecob R A, Leanage R, Raeburn J A, Young I D. Holt-Oram syndrome: a clinical genetic study. J Med. Genet. 1996; 33:300-7.
8. Yu J, Cheng Y Y, Tao Q, Cheung K F, Lam C N, Geng H, Tian L W, Wong Y P, Tong J H, Ying J M, Jin H, To K F, Chan F K, Sung J J. Methylation of protocadherin 10, a novel tumor suppressor, is associated with poor prognosis in patients with gastric cancer. Gastroenterology. 2009; 136:640-51.
9. Yu J, Tao Q, Cheng Y Y, Lee K Y, Ng S S, Cheung K F, Tian L, Rha S Y, Neumann U, Röcken C, Ebert M P, Chan F K, Sung J J. Promoter methylation of the Wnt/beta-catenin signaling antagonist Dkk-3 is associated with poor survival in gastric cancer. Cancer. 2009; 115:49-60.
10. Papaioannou V E, Silver L M. The T-box gene family. Bioessays. 1998; 20:9-19.
11. Finotto S. T-cell regulation in asthmatic diseases. Chem Immunol Allergy. 2008; 94:83-92.
12. Nemer M. Genetic insights into normal and abnormal heart development. Cardiovasc Pathol. 2008; 17:48-54.
13. Cai C L, Zhou W, Yang L, Bu L, Qyang Y, Zhang X, Li X, Rosenfeld M G, Chen J, Evans S. T-box genes coordinate regional rates of proliferation and regional specification during cardiogenesis. Development. 2005; 132:2475-87.

SUMMARY

The applicants have identified a novel preferentially methylated gene, T-box transcription factor 5 (TBX5) (also known as T-box 5), in human colon cancer.

In a first embodiment, there is disclosed a method for diagnosing or providing a prognosis for colon cancer in a biological sample. The method may comprise the step of: detecting methylation of a patient sample sequence of at least 15 consecutive base pairs, within a contiguous sequence at least 95% similar to the region consisting of SEQ ID NO:1; wherein significant methylation level is indicative of cancer presence in the sample.

In alternative embodiments, the target sequence may be at least 50 base pairs long and contain a plurality of CpG base pairs. The method may further comprise comparing the methylation level of the patient sample DNA with methylation level of non-cancerous cells to thereby detect the presence of colon cancer. The determining may comprise treating the sample with a reagent that differentially modifies methylated and unmethylated DNA. The reagent may comprise a restriction enzyme that preferentially cleaves methylated DNA or that preferentially cleaves unmethylated DNA. The determining may comprise treating the sample with sodium bisulphate. The determining may comprise the steps of: amplifying DNA using primers flanking a CpG-containing genomic sequence, the genomic sequence may be contained within SEQ ID NO:1. The amplifying may use the polymerase chain reaction.

In alternative embodiments; the target sequence may be at least 25 base pairs long. The sample may comprise colon tissue. The detecting may comprise amplifying the region. The amplifying may use the polymerase chain reaction. The detecting may comprise using a primer selected from the group consisting of alternative primer sequences.

In another embodiment, there is disclosed a composition for suppressing colon cancer in a patient. The composition may comprise a biologically acceptable expression vector for expressing a portion of the TBX5 gene in the patient's cells.

In alternative embodiments, the vector may be suitable to direct expression of TBX5 protein in patient's cells.

In another embodiment, there is disclosed a method for inhibiting colon cancer in a subject. The method may comprise exposing the cells of the subject to the compositions disclosed herein.

In alternative embodiments, the vector may be delivered by viral transduction.

In another embodiment, there is disclosed a method for assessing the progress of colon cancer in a subject. The method may comprise the steps of: detecting methylation of a patient sample sequence of at least 10 consecutive base pairs, within a contiguous sequence at least 95% similar to the region consisting SEQ ID NO:1; comparing the results to a reference; and using the results to determine the progress of the colon cancer in the subject.

In an embodiment there is disclosed a method for detecting colon cancer in a biological sample, said method comprising the step of: detecting methylation of a patient sample comprising a target sequence of at least 15 consecutive base pairs of genomic DNA, within a contiguous sequence at least 95% similar to SEQ ID NO:1; wherein significant methylation level is indicative of cancer presence in the sample.

In an alternative embodiment the target sequence is at least 50 base pairs long and contains a plurality of CpG base pairs.

In an alternative embodiment the method may further comprise comparing the methylation level of the target sequence in a subject with the methylation level of the target sequence in non-cancerous cells.

In an alternative embodiment the determining comprises treating the sample with a reagent that differentially modifies methylated and unmethylated DNA.

In an alternative embodiment the method further comprises treating the DNA with a reagent that preferentially cleaves methylated DNA.

In an alternative embodiment the determining comprises treating the sample with sodium bisulphate.

In an alternative embodiment the determination is performed by combined bisulfite restriction analysis (COBRA).

In an alternative embodiment the sample is a blood sample or a stool sample.

In an alternative embodiment the determining comprises the steps of: a) amplifying DNA from the sample with primers flanking CpG-containing genomic sequence, wherein the genomic sequence is comprised within SEQ ID NO:1; and comparing the methylation level of the amplified portion of the genomic sequence in the sample with the methylation level of the genomic sequence in a non-cancerous sample, to thereby detect the presence of colon cancer.

In an alternative embodiment the reagent that preferentially cleaves methylated DNA is a restriction enzyme.

In an alternative embodiment the amplifying uses the polymerase chain reaction.

In an alternative embodiment the detecting uses a primer or probe selected from the group consisting of: SEQ ID NO:4, SEQ ID NO:5, SEQ ID NO:8, SEQ ID NO:9, SEQ ID NO:10, and SEQ ID NO:11.

In an alternative embodiment the there is disclosed a method for inhibiting the development of colon cancer cells, the method comprising the step of: 1 expressing a biologically effective portion of SEQ ID NO:13 in the cancer cells to thereby inhibit the growth of the cells.

In an alternative embodiment the expressing comprises demethylating a DNA sequence in the said colon cancer cells with at least 95% sequence similarity over at least 15 contiguous base pairs to SEQ ID NO:1.

In an alternative embodiment the expressing comprises introducing into said cells an isolated DNA molecule comprising a TBX5 coding sequence operatively linked to promoter.

In an alternative embodiment the there is disclosed an isolated nucleic acid molecule comprising a sequence with at least 95% sequence similarity over at least 15 contiguous base pairs to SEQ ID NO:1.

In an alternative embodiment the isolated nucleic acid molecule further comprises a vector.

In an alternative embodiment of the isolated nucleic acid molecule the sequence is demethylated In an alternative embodiment there is disclosed a method for detecting colon cancer in a biological sample, the method comprising the steps of: amplifying a region of the DNA in the sample with at least 95% similarity over at least 15 contiguous base pairs to a portion of SEQ ID NO:1; cleaving the amplified DNA with a reagent that preferentially cleaves methylated DNA; and comparing the cleavage products to the cleavage products an isolated DNA molecule to thereby detect colon cancer in the sample.

In an alternative embodiment there is disclosed a kit for detecting colon cancer in a biological sample, the kit comprising: two primers suitable to amplify a region of the DNA in the sample with at least 95% similarity over at least 15 contiguous base pairs to a portion of SEQ ID NO:1.

In an embodiment there is disclosed a method for detecting colon cancer in a biological sample, said method comprising the step of: detecting the level in the sample of an RNA sequence having at least 95% sequence similarity to a region of at least 15 contiguous base pairs of SEQ ID NO:13, wherein a significantly lower amount of the said sequence in the sample relative to a non-cancerous control is indicative of presence of colon cancer in the biological sample.

In embodiments the sequence similarities may be greater than 90%, or greater than 95%, or greater than 99%, and may extend over a region of 15, 20, 25, 30, 40, 50 or more bases.

Features and advantages of the subject matter hereof will become more apparent in light of the following detailed description of selected embodiments, as illustrated in the accompanying figures. As will be realized, the subject matter disclosed and claimed is capable of modifications in various respects, all without departing from the scope of the claims. Accordingly, the drawings and the description are to be regarded as illustrative in nature, and not as restrictive and the full scope of the subject matter is set forth in the claims.

BRIEF DESCRIPTION OF THE DRAWINGS

FIG. 1. (A) A typical CpG island (CGI) spans the promoter region of TBX5 exon 1. Each vertical bar represents a single CpG site. The transcription start site (TSS) is indicated by a curved arrow. A region for combined bisulfite restriction analysis (COBRA) and bisulfite genomic sequencing (BGS) is shown. BstUI digestive sites are indicated.

FIG. 1. (B) TBX5 was frequently silenced or down-regulated in colon cancer cell lines, but readily expressed in normal colon tissues by semi-quantitative RT-PCR. Methylation of TBX5 was determined by COBRA The undigested fragment (upper band) represents the unmethylated DNA (U). The digested fragments represent the methylated DNA (M).

FIG. 1. (C) Detailed BGS analysis confirmed the methylation status of the TBX5 in colon cancer cell lines and in normal colon tissues. Five to six colonies of cloned BGS-PCR products from each bisulfite-treated DNA sample were sequenced and each is shown as an individual row, representing a single allele of the promoter CpG island analyzed. One circle indicates one CpG site. Filled circle, methylated; Open circle, unmethylated.

FIG. 1. (D) The mRNA expression of TBX5 was restored after treatment with demethylation agent 5-Aza-2'-deoxycytidine (5-Aza).

FIGS. 2(A1)-2(B3) show TBX5 effects on tumour cell viability and clonogenicity in an embodiment.

FIGS. 3(A1)-3(B) show TBX5 effects on apoptosis of SW620 cells and migration rates of SW620 cells in an embodiment.

FIGS. 4(A1)-4(B) shows the relationships between methylation of the TBX5 gene, the occurrence of colon cancer, and patient survival in an embodiment.

DETAILED DESCRIPTION OF EMBODIMENTS

Terms

In this disclosure the following terms have the meanings set forth below:

In this disclosure the term "or" is generally employed in its sense including "and/or" unless the content clearly dictates otherwise.

In this disclosure, the term "biomarker" or "marker" means a substance such as a gene, a measurement of a variable related to a disease that may serve as an indicator or predictor of that disease. Biomarkers or markers are parameters from which the presence or risk of a disease can be inferred, rather than being a measure of the disease itself.

In this disclosure the terms "nucleic acid", "nucleic acid sequence," and the like mean polynucleotides, which may be gDNA, cDNA or RNA and which may be single-stranded or double-stranded. The term also includes peptide nucleic acid (PNA), or any chemically DNA-like or RNA-like material. "cDNA" refers to copy DNA made from mRNA that is naturally occurring in a cell. "gDNA" refers to genomic DNA. Combinations of the same are also possible (i.e., a recombinant nucleic acid that is part gDNA and part cDNA).

In this disclosure the terms "operably associated" and "operably linked," mean functionally coupled nucleic acid sequences.

In this disclosure the terms "stringent hybridization conditions" and "high stringency" refer to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993) and will be readily understood by those skilled in the art. Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42.°C., or, 5×SSC, 1% SDS, incubating at 65° C., with wash in 0.2×SSC, and 0.1% SDS at 65.degree. C. Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous references, e.g., Current Protocols in Molecular Biology, ed. Ausubel, et al.

For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec-2 min., an annealing phase lasting 30 sec.-2 min., and an extension phase of about 72° C. for 1-2 min. Protocols and guidelines for low and high stringency amplification reactions are well known in the art and are provided, e.g., in Innis et al. (1990) PCR Protocols, A Guide to Methods and Applications, Academic Press, Inc. N.Y.).

In this disclosure the term "polypeptide" means a polypeptide encoded by a nucleic acid molecule.

In this disclosure the terms "gene expression" and "protein expression" mean and includes any information pertaining to the amount of gene transcript or protein present in a sample, as well as information about the rate at which genes, RNA or proteins are being expressed or are accumulating or being degraded (e.g., reporter gene data, data from nuclear runoff experiments, pulse-chase data etc.). Certain kinds of data might be viewed as relating to both gene and protein expression. For example, protein levels in a cell are reflective of the level of protein as well as the level of transcription, and such data is intended to be included by the phrase "gene or protein expression information." Such information may be given in the form of amounts per cell, amounts relative to a control gene or protein, in unitless measures, etc.; the term "information" is not to be limited to any particular means of representation and is intended to mean any representation that provides relevant information. The term "expression levels" refers to a quantity reflected in or derivable from the gene or protein expression data, whether the data is directed to gene transcript accumulation or protein accumulation or protein synthesis rates, etc.

In this disclosure the term "polypeptide" means a molecule comprised of two or more amino acids, preferably more than three. Its exact size will depend upon many factors.

In this disclosure the term "oligonucleotide" means a molecule comprised of two or more nucleotides, preferably more than three. Its exact size will depend upon many factors which, in turn, depend upon the ultimate function and use of the oligonucleotide. In particular embodiments an oligonucleotide may have a length of about 10 nucleotides to 100 nucleotides or any integer therebetween. In embodiments oligonucleotides may be about 10 to 30 nucleotides long, or may be between about 20 and 25 nucleotides long. In embodiments an oligonucleotide may be greater than about 10, 11, 12, 13, 14, 15, 16, 17, 18, 19, 20, 21, 22, 23, 24, or 25 nucleotides long for specificity. In certain embodiments oligonucleotides shorter than these lengths may be suitable.

In this disclosure the term "primer" means an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA or RNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and the method used. For example, for diagnostic and prognostic applications, depending on the complexity of the target sequence, the oligonucleotide primer typically contains at least or more than about 10, or 15, or 20, or 25 or more nucleotides, although it may contain fewer nucleotides or more nucleotides. The factors involved in determining the appropriate length of primer are readily known to one of ordinary skill in the art.

In this disclosure the term "primer pair", means a pair of primers which hybridize to opposite strands a target DNA molecule, to regions of the target DNA which flank a nucleotide sequence to be amplified.

In this disclosure the term "primer site", means the area of the target DNA to which a primer hybridizes.

In this disclosure, the nucleic acids, polynucleotides, proteins, and polypeptides described and claimed refer to all forms of nucleic acid and amino acid sequences, including but not limited to genomic nucleic acids, pre-mRNA, mRNA, polypeptides, polypeptides, polymorphic variants, alleles, mutants, and interspecies homologs that:

(1) have or encode an amino acid sequence that has greater than about 60% amino acid sequence identity, 65%, 70%, 75%, 80%, 85%, 90%, preferably 91%, 92%, 93%, 94%, 95%, 96%, 97%, 98% or 99% or greater amino acid sequence identity, preferably over a region of at least about 25, 50, 100, 200, 500, 1000, or more amino acids, to a polypeptide encoded by a referenced nucleic acid or an amino acid sequence described herein;

(2) specifically bind to or encode polypeptides that specifically bind to antibodies, e.g., polyclonal antibodies, raised against an immunogen comprising a referenced amino acid sequence, immunogenic fragments thereof, and conservatively modified variants thereof;

(3) specifically hybridize under stringent hybridization conditions to a disclosed nucleic acid sequence or to a nucleic acid sequence encoding a disclosed amino acid sequence, and conservatively modified variants thereof;

(4) have a nucleic acid sequence that has greater than about 95%, preferably greater than about 96%, 97%, 98%, 99%, or higher nucleotide sequence identity, preferably over a region of at least about 15, 25, 50, 100, 200, 500, 1000, or more nucleotides, to a reference nucleic acid sequence.

A polynucleotide or polypeptide sequence is typically from a mammal including, but not limited to, primate, e.g., human; rodent, e.g., rat, mouse, hamster; cow, pig, horse, sheep, or any mammal. In particular embodiments the polynucleotide and polypeptide sequences disclosed are from humans. The nucleic acids and proteins of the invention include both naturally occurring or recombinant molecules.

In this disclosure the term "biological sample" or "sample" includes sections of tissues such as biopsy and autopsy samples, and frozen sections taken for histologic purposes, or processed forms of any of such samples. Biological samples include blood and blood fractions or products (e.g., serum, plasma, platelets, red blood cells, and the like), sputum or saliva, lymph and tongue tissue, cultured cells, e.g., primary cultures, explants, and transformed cells, stool, urine, stomach biopsy tissue etc. A biological sample is typically obtained from a eukaryotic organism, which may be a mammal, may be a primate and may be a human subject.

In this disclosure the term "biopsy" refers to the process of removing a tissue sample for diagnostic or prognostic evaluation, and to the tissue specimen itself. Any biopsy technique known in the art can be applied to the diagnostic and prognostic methods of the present invention. The biopsy technique applied will depend on the tissue type to be evaluated (e.g., tongue, colon, prostate, kidney, bladder, lymph node, liver, bone marrow, blood cell, stomach tissue, etc.) among other factors. Representative biopsy techniques include, but are not limited to, excisional biopsy, incisional biopsy, needle biopsy, surgical biopsy, and bone marrow biopsy and may comprise colonoscopy. A wide range of biopsy techniques are well known to those skilled in the art who will choose between them and implement them with minimal experimentation.

In this disclosure the term "isolated" nucleic acid molecule means a nucleic acid molecule that is separated from other nucleic acid molecules that are usually associated with the isolated nucleic acid molecule. Thus, an "isolated" nucleic acid molecule includes, without limitation, a nucleic acid molecule that is free of sequences that naturally flank one or both ends of the nucleic acid in the genome of the organism from which the isolated nucleic acid is derived (e.g., a cDNA or genomic DNA fragment produced by PCR or restriction endonuclease digestion). Such an isolated nucleic acid molecule is generally introduced into a vector (e.g., a cloning vector, or an expression vector) for convenience of manipulation or to generate a fusion nucleic acid molecule. In addition, an isolated nucleic acid molecule can include an engineered nucleic acid molecule such as a recombinant or a synthetic nucleic acid molecule. A nucleic acid molecule existing among hundreds to millions of other nucleic acid molecules within, for example, a nucleic acid library (e.g., a cDNA, or genomic library) or a portion of a gel (e.g., agarose, or polyacrylamine) containing restriction-digested genomic DNA is not to be considered an isolated nucleic acid.

In this disclosure a "cell" may be isolated, may be comprised in a group of cells, may be in culture, or may be comprised in a living subject and may be a mammalian cell and may be a human cell. Similarly "tissue" may comprise any number of cells and may be comprised in a living subject more may be isolated therefrom.

In this disclosure "cancer" means and includes any malignancy, or malignant cell division or malignant tumour, or any condition comprising uncontrolled or inappropriate cell proliferation and includes without limitation any disease characterized by uncontrolled or inappropriate cell proliferation.

In this disclosure the terms "colon cancer" and "colorectal cancer" have the same meaning and mean a cancer of the colon, or rectum and include cells characteristic of colorectal cancer. Without limitation, colon cancers may be adenocarcinomas, leiomyosarcomas, lymphomas, melanomas, and neuroendocrine tumors.

In this disclosure the term "colon cancer cell" or "colorectal cancer cell" means a cell characteristic of colon cancer, and includes cells which are precancerous.

In this disclosure the term "precancerous" means a cell which is in the early stages of conversion to a cancer cell or which is predisposed for conversion to a cancer cell. Such cells may show one or more phenotypic traits characteristic of the cancerous cell.

In this disclosure the term "purified," or "substantially purified" means nucleic acids or polypeptides separated from their natural environment so that they are at least about 75%, 80, 85, 90 or 95% of total nucleic acid or polypeptide or organic chemicals in a given sample. Protein purity is assessed herein by SDS-PAGE and silver staining. Nucleic acid purity is assessed by agarose gel and EtBr staining.

In this disclosure the term "detection" means any process of observing a marker, or a change in a marker (such as for example the change in the methylation state of the marker, or the level of expression of nucleic acid or protein sequences), in a biological sample, whether or not the marker or the change in the marker is actually detected. In other words, the act of probing a sample for a marker or a change in the marker, is a "detection" even if the marker is determined to be not present or below the level of sensitivity. Detection may be a quantitative, semi-quantitative or non-quantitative observation and may be based on a comparison with one or more control samples. It will be understood that detecting a colon cancer as disclosed herein includes detecting precancerous cells that are beginning to or will, or have an increased predisposition to develop into colon cancer cells. Detecting a colon cancer also includes detecting a likely probability of mortality or a likely prognosis for the condition.

In this disclosure the term "expression vector" means a replicable DNA construct used to express DNA which encodes a desired protein or RNA sequence and which includes a transcriptional unit comprising an assembly of (1) genetic element(s) having a regulatory role in gene expression, for example, promoters, operators, or enhancers, operatively linked to (2) a DNA sequence encoding a desired protein (in this case, an TBX5 protein) which is transcribed into mRNA and translated into protein, and (3) appropriate transcription and translation initiation and termination sequences. The choice of promoter and other regulatory elements generally varies according to the intended host cell. In general, expression vectors of utility in recombinant DNA techniques are often in the form of "plasmids" which refer to circular double stranded DNA loops which, in their vector form are not bound to the chromosome or in the form of viral sequences which may or may not integrate into the chromosomes. A wide range of expression vectors will be readily recognised and used by those skilled in the art.

In this disclosure the terms "homology", "identity" and "similarity" mean sequence similarity between two peptides or between two nucleic acid molecules. They can each be determined by comparing a position in each sequence which may be aligned for purposes of comparison. When an equivalent position in the compared sequences is occupied by the same base or amino acid, then the molecules are identical at that position; when the equivalent site occupied by the same or a similar amino acid residue (e.g., similar in steric and/or electronic nature), then the molecules can be referred to as homologous (similar) at that position. Expression as a percentage of homology/similarity or identity refers to a function of the number of identical or similar amino acids at positions shared by the compared sequences. A sequence which is "unrelated or "non-homologous" shares less than 40% identity, preferably less than 25% identity with a sequence of the present invention. In comparing two sequences, the absence of residues (amino acids or nucleic acids) or presence of extra residues also decreases the identity and homology/similarity. In particular embodiments two or more sequences or subsequences may be considered substantially or significantly homologous, similar or identical if their sequences are about 60% identical, or are about 65%, 70%, 75%, 80%, 85%, 90%, 91%, 92%, 93%, 94%, 95%, 96%, 97%, 98%, 99%, or higher over a specified region, when compared and aligned for maximum correspondence over a comparison window or designated region, as measured using a BLAST or BLAST 2.0 sequence comparison algorithms with default parameters described below, or by manual alignment and visual inspection such as provided on-line by the National Center for Biotechnology Information (NCBI). This definition also refers to, or may be applied to, the compliment of a test sequence. Thus, to the extent the context allows, for instance where a nucleotide sequence may be expected to naturally occur in a DNA duplex, or may naturally occur in the form of either or both of the complementary strands, then a nucleotide sequence that is complimentary to a specified target sequence or its variants, is itself deemed "similar" to the target sequence and a reference to a "similar" nucleic acid sequence includes both the single strand sequence, its complimentary sequence, the double stranded complex of the strands, sequences able to encode the same or similar polypeptide products, and any permissible variants to any of the foregoing. Circumstances where similarity must be limited to an analysis of the sequence of a single nucleic acid strand may include for example the detection and quantification of the expression of a specific RNA sequence or coding sequence within a cell. The definition also includes sequences that have deletions and/or additions, as well as those that have substitutions. In embodiments identity or similarity may exist over a region that is at least about 10, 11, 12, 13, 14, 15, 16, 17, 18, 19, 10, 21, 22, 23, 24, 25 or more amino acids or nucleotides in length, or over a region that is more than about 10, 15, 20, 25, 30, 35, 40, 45, 50, 55, 60, 65, 70, 75, 80, 85, 90, 95 or more than about 100 amino acids or nucleotides in length.

In this disclosure the term "methylation-sensitive PCR" (i.e., MSP) means a polymerase chain reaction in which amplification of the compound-converted template sequence is performed. Two sets of primers are designed for use in MSP. Each set of primers comprises a forward primer and a reverse primer. One set of primers, called methylation-specific primers, will amplify the compound-converted template sequence if C bases in CpG dinucleotides within the target DNA are methylated. Another set of primers, called unmethylation-specific primers, will amplify the compound-converted template sequences if C bases in CpG dinucleotides within the target DNA are not methylated.

In this disclosure the terms "inhibit" and "suppress" where used with reference to cancer cells or the growth or development thereof, mean and include any effects that result in or comprise slowing or preventing growth or cell division of the cells, killing the cells, disabling the cells, and in any way reducing the viability, rate of division or longevity of the cells and includes any metabolic changes which change the characteristics of the cells in ways more characteristic of benign rather than malignant cell populations.

In this disclosure "Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding. Antibodies can be polyclonal or monoclonal, derived from serum, a hybridoma or recombinantly cloned, and can also be chimeric, primatized, or humanized. Antibodies exist, e.g., as intact immunoglobulins or as a number of well-characterized fragments which can be produced by digestion with various peptidases. The term antibody, as used herein, includes both complete antibodies and also antibody fragments either produced by the modification of whole antibodies, or synthesized de novo using recombinant DNA methodologies (e.g., single chain Fv) or those identified using phage display libraries.

In this disclosure the term "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies can be selected to obtain only those polyclonal antibodies that are specifically immunoreactive with the selected antigen and not with other proteins.

This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein.

In this disclosure the term "amplify", means a process whereby multiple copies are made of one particular locus of a nucleic acid, such as genomic DNA or cDNA. Amplification can be accomplished using any one of a number of known means, including but not limited to the polymerase chain reaction (PCR), transcription based amplification and strand displacement amplification (SDA).

In this disclosure the term "polymerase chain reaction" or "PCR", means, a technique in which cycles of denaturation, annealing with primer, and extension with DNA polymerase are used to amplify the number of copies of a target DNA sequence by approximately $10^6$ times or more. The polymerase chain reaction process for amplifying nucleic acid is covered by U.S. Pat. Nos. 4,683,195 and 4,683,202.

In this disclosure the term "conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

In this disclosure a "label" or a "detectable moiety" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins which can be made detectable, e.g., by incorporating a radiolabel into the peptide or used to detect antibodies specifically reactive with the peptide.

In this disclosure the term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

Exclusion of Certain Sequences:

It will be understood that in particular embodiments individual examples of sequences, probes, primers, polypeptides or the like may be excluded.

Detection of Nucleic Acids and Polypeptides:

A range of methods for the detection of specific nucleic acid sequences and polypeptides and their application will be readily apparent to those skilled in the art.

Nucleic acid molecules and polypeptides can be detected using a number of different methods. Methods for detecting nucleic acids include, for example, PCR and nucleic acid hybridizations (e.g., Southern blot, Northern blot, or in situ hybridizations). Specifically, oligonucleotides (e.g., oligonucleotide primers) capable of amplifying a target nucleic acid can be used in a PCR reaction. PCR methods generally include the steps of obtaining a sample, isolating nucleic acid (e.g., DNA, RNA, or both) from the sample, and contacting the nucleic acid with one or more oligonucleotide primers that hybridize(s) with specificity to the template nucleic acid under conditions such that amplification of the template nucleic acid occurs. In the presence of a template nucleic acid, an amplification product is produced. Conditions for amplification of a nucleic acid and detection of an amplification product are known to those of skill in the art. A range of modifications to the basic technique of PCR also have been developed, including but not limited to anchor PCR, RACE PCR, RT-PCR, and ligation chain reaction (LCR). A pair of primers in an amplification reaction must anneal to opposite strands of the template nucleic acid, and should be an appropriate distance from one another such that the polymerase can effectively polymerize across the region and such that the amplification product can be readily detected using, for example, electrophoresis. Oligonucleotide primers can be designed using, for example, a computer program such as OLIGO (Molecular Biology Insights Inc., Cascade, Colo.) to assist in designing primers that have similar melting temperatures. Typically, oligonucleotide primers are 10 to 30 or 40 or 50 nucleotides in length (e.g., 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length), but can be longer or shorter if appropriate amplification conditions are used.

In this disclosure the term "standard amplification conditions" refers to the basic components of an amplification reaction mix, and cycling conditions that include multiple cycles of denaturing the template nucleic acid, annealing the oligonucleotide primers to the template nucleic acid, and extension of the primers by the polymerase to produce an amplification product.

Detection of an amplification product or a hybridization complex is usually accomplished using detectable labels. The term "label" with regard to a nucleic acid is intended to encompass direct labeling of a nucleic acid by coupling (i.e., physically linking) a detectable substance to the nucleic acid, as well as indirect labeling of the nucleic acid by reactivity with another reagent that is directly labeled with a detectable substance. Detectable substances include various enzymes, prosthetic groups, fluorescent materials, luminescent materials, bioluminescent materials, and radioactive materials. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$, or $^{3}H$. An example of indirect labeling includes end-labeling a nucleic acid with biotin such that it can be detected with fluorescently labeled streptavidin.

Specific polypeptide sequences may be detected using polyclonal or monoclonal antibodies which can be prepared in conventional ways as will be readily understood and applied by those skilled in the art. Those skilled in the art will readily identify and prepare and raise antibodies to desirable polypeptide sequences to implement the subject matter disclosed and claimed.

The term "probe" with regard to nucleic acid sequences is used in its ordinary sense to mean a selected nucleic acid sequence that will hybridise under specified conditions to a target sequence and may be used to detect the presence of such target sequence. It will be understood by those skilled in the art that in some instances probes may be also be useable as primers, and primers may useable as probes.

Methylation:

In this disclosure, DNA "methylation" refers to the addition of a methyl group to the 5 position of cytosine (C), typically (but not necessarily) in the context of CpG (a cytosine followed by a guanine) dinucleotides. As used herein, "an increased methylation level" or "a significant methylation level" refers to the presence of at least one methylated C nucleotide in a DNA sequence where the corresponding C is not methylated in a normal control sample (such as a DNA sample extracted from a non-cancerous cell or tissue sample, or a DNA sample that has been treated to the methylation on DNA residutes), in some embodiments at least 2, 3, 4, 5, 6, 7, 8, 9, 10 or more Cs may be methylated at locations where the Cs are unmethylated in a control DNA sample.

In embodiments, DNA methylation alterations can be detected using a number of different methods. Methods for detecting DNA methylation include, for example, methylation-sensitive restriction endonucleases (MSREs) assay by either southern or polymerase chain reaction (PCR) analysis, methylation specific or methylation sensitive-PCR (MS-PCR), methylation-sensitive single nucleotide primer extension (Ms-SnuPE), high resolution melting (HRM) analysis, bisulifte sequencing, pyrosequencing, methylation-specific single-strand conformation analysis (MS-SSCA), combined bisulifte restriction analysis (COBRA), methylation-specific denaturing gradient gel electrophoresis (MS-DGGE), methylation-specific melting curve analysis (MS-MCA), methylation-specific denaturing high-performance liquid chromatography (MS-DHPLC), methylation-specific microarray (MSO). These assays can be either PCR analysis, quantitative analysis with fluorescence labelling or southern blot analysis. In embodiments the degree of methylation of a sequence may be determined using a methylation sensitive DNA cleaving reagent which may be a restriction enzyme and for example may be AatII, AciI, AclI, AgeI, AscI, Asp718, AvaI, BbrP1, BceAI, BmgBI, BsaAI, BsaHI, BsiEI, BsiWI, BsmBI, BspDI, BsrFI, BssHII, BstBI, BstUI, ClaI, EagI, EagI-HF™, FauI, FseI, FspI, HaeII, HgaI, HhaI, HinP1I, HpaII, Hpy99I, HpyCH4IV, KasI, MluI, NarI, NgoMIV, NotI, NotI-HF™, NruI, Nt.BsmAI, PaeR7I, PspXI, PvuI, RsrII, SacII, SalI, SalI-HF™, SfoI, SgrAI, SmaI, SnaBI or TspMI.

Articles of Manufacture

This disclosure encompasses articles of manufacture (e.g., kits) that contain one or more nucleic acid molecules, or one or more vectors that encode a nucleic acid molecule. Such nucleic acid molecules are formulated for administration as described herein, and can be packaged appropriately for the intended route of administration. For example, a nucleic acid molecule or a vector encoding a nucleic acid molecule can be contained within or accompanied by a pharmaceutically acceptable carrier.

Kits of according to embodiments can include additional reagents (e.g., buffers, co-factors, or enzymes). Pharmaceutical compositions according to embodiments can include instructions for administering the composition to an individual. Kits may also contain a control sample or a series of control samples that can be assayed and compared to the biological sample. Each component of a kit may be enclosed within an individual container and all of the various containers are within a single package.

Compositions and Delivery of Compositions to Target Cells

In certain embodiments there are disclosed compositions for delivery to target cells. It will be understood that the compositions used in particular embodiments may be used in combination with suitable pharmaceutically acceptable carriers or excipients and may be used in any suitable dosage forms. Those skilled in the art will readily identify, select from, and use the foregoing to suit the circumstances in question. Where a cell to be treated is comprised in the body of a subject the methods disclosed may be implemented and the compositions disclosed may be delivered to the cell in any conventional ways including without limitation the delivery of the tetrose or prodrug, orally, parentally, enterally, intramuscularly, subcutaneously, intravenously, or by inhalation and may be delivered in combination with suitable carriers or excipients, in suitable dosage forms including without limitation tablets, capsules, subdermal pumps or other routes useful to achieve an effect. Alternative delivery methods may include osmotic pumps, implantable infusion systems, intravenous drug delivery systems, and refillable implantable drug delivery systems. Delivery by inhalation may comprise delivery using nebulizers, metered dose inhalers, powder inhalers, all of which are familiar to those skilled in the art. Suitable methods, compositions and routes of delivery will be readily recognised and implemented by those skilled in the art.

Embodiments

In embodiments there are disclosed TBX5 genomic sequences, which may be TBX5 promoter sequences, and whose methylation may be correlated with the presence or progress or prognosis of colon cancer, and which may be useable as a diagnostic or prognostic marker for colon cancer. In embodiments it may be possible to prevent or inhibit the progression of colon cancer by demethylating the diagnostic or prognostic sequences. The embodiments and examples are described with reference to FIGS. 1 through 4 and Table 3 and are further illustrated by examples presented herein. Further explanation of particular terms used in describing the embodiments is provided above and the use of such terms below incorporates all such additional explanation, and also includes all further explanation presented in the Examples.

The TBX5 promoter region comprised in or comprising a marker or markers of an embodiment is shown in FIG. 1A, and Table 3 and is generally designated SEQ ID NO:1 and may comprise basepairs −605 through −902 relative to the transcription start site of the human TBX5 gene. This region includes CpG nucleotide pairs which may be methylated. The applicants have found that methylation of the TBX5 promoter sequences in a subject may be associated with the presence of colon cancer, and may be associated with poor prognosis for such cancer and may be associated with decreased life expectancy. Broadly, it was found that the TBX5 gene promoter was partly or highly methylated in colon cancer tissues compared with adjacent non-tumor tissues, but was not methylated in normal controls. It will be understood that in alternative embodiments particular portions of SEQ ID NO:1 may be used as markers, and may be as short or as long as 15, 20, 25, 30, 35, 40, 45, 50 or more or fewer base pairs. It will be understood that the complement of SEQ ID NO:1 can be used instead of SEQ ID NO:1 itself and that any reference herein indicating SEQ ID NO:1 includes its complementary sequence.

In an alternative embodiment there is disclosed a method for detecting colon cancer in a biological sample. The method may comprise the step of detecting methylation of a patient sample comprising a target sequence of at least 15 consecutive base pairs of genomic DNA, within a contiguous sequence at least 95% similar to SEQ ID NO:1 (corresponding to bases −902 bp to −605 bp of the human TBX5 gene); wherein a significant methylation level is indicative of cancer presence in the sample. It will be appreciated that in variants of the embodiment, the level of similarity in the target sequence may be greater than about 90%, 91%, 92%, 93%, 94%, 95%, 96%, 97%, 98%, 99%, or may be 100% and that the target sequence may be greater than about 15, 20, 25, 30, 35, 40, 45, 50 or more base pairs long. In embodiments the region of similarity used as a marker may comprise one or more CpG base pairs and may comprise a plurality of CpG base pairs. As explained herein the detecting may be accomplished in a range of ways all readily understood by those skilled in the art. Similarly as set out herein methylation, or significant methylation may be partial or complete.

In embodiments the method may further comprise comparing the methylation level of the target sequence in a subject with the methylation level of the target sequence in non-cancerous cells, or with unmethylated target sequence. In embodiments the determining may comprise treating the sample with a reagent that differentially modifies methylated and unmethylated DNA. The reagent that differentially modifies may convert unmethylated cytosine to uracil whereas methylated cytosine remains unchanged. In embodiments, a restriction enzyme may preferentially cleave the unchanged CpG sites and in alternative embodiments may preferentially cleave changed CpG sites. In embodiments the determining may comprise treating the sample with sodium bisulphate and may be performed by combined bisulfite restriction analysis (COBRA). In embodiments the biological sample may be a blood sample or may be a stool sample.

In embodiments the determining may comprise the steps of amplifying DNA from the sample with primers selective for a CpG-containing genomic sequence, wherein the genomic sequence is, or is comprised within, SEQ ID NO:1; and comparing the methylation level of the amplified portion of the genomic sequence in the sample with the methylation level of the genomic sequence in a non-cancerous sample or a non methylated sample to thereby detect the presence of colon cancer. In embodiments the reagent that preferentially cleaves unmethylated DNA may be a restriction enzyme. In embodiments, amplifying the DNA may use the polymerase chain reaction.

In embodiments the step of detecting may comprise amplifying and may comprise using a primer or probe selected from the group consisting of: SEQ ID NOS:4, 5, 8, 9, 10 and 11.

In further embodiments there are disclosed kits for detecting colon cancer, the kits comprising primers disclosed in the other embodiments. Such kits may also comprise isolation buffers, reagents, standard and control samples and instructions on the use of the foregoing.

In a further embodiment there is disclosed a method for detecting colon cancer in a biological sample, the method comprising the step of: detecting the level in the sample of an RNA sequence having at least 95% sequence similarity to a region of at least 15 contiguous base pairs of an mRNA transcript of the TBX5 gene (SEQ ID NO:13) wherein a significantly lower amount of the said sequence in the sample relative to a non-cancerous control sample is indicative of the presence of colon cancer in the biological sample. In embodiments the similarity may be assessed over a region at least about 15, 20, 25, 30, 35, 40, 45, 50 or more base pairs long. In embodiments the sample may comprise colon tissue, the detecting may comprise amplifying the region, and the sample may be a blood or stool sample. In embodiments the transcript may be detected using suitable amplification primers and in embodiments suitable primers may have sequences selected from the group consisting of SEQ ID NOS:2, 3, and 14 through 27, or primer pairs A though G, or the primer pair consisting of SEQ ID NOS:2 and 3.

Further Alternative Embodiments

In embodiments it was found that restoration of TBX5 expression in the colorectal cancer cells significantly inhibited colony formation and cell proliferation and induced apoptosis. Ectopic expression of TBX5 in colon cancer cells decreased migration ability. Thus, it is apparent that expressing the TBX5 sequences in colon cancer cells may inhibit growth and development of the cells and of tumors comprising such cells. In embodiments the restoration of TBX5 expression may be achieved in cell lines CaCO2 and SW620, but those skilled in the art will recognise that such restoration of expression can be readily achieved in a range of other cell lines and in cells in vivo, and in a subject, and in a human subject and will readily identify and implement methods, vectors and strategies to achieve such restored expression. Those skilled in the art will recognise that restored expression may utilise exogenous introduction of a TBX5 transcription unit (whether natural or artificially constructed), or may utilise reactivation of the endogenous TBX5 gene, or may utilise the introduction of a TBX5 gene from a different organism or that has been modified or that is associated with heterologous sequences suitable to drive the expression of the TBX5 coding sequences or protein or portions thereof.

Thus in embodiments there is disclosed a method for inhibiting the development of colon cancer cells, the method comprising the step of expressing a biologically effective portion of the TBX5 gene in the cancer cells to thereby inhibit the growth of the cells. It will be understood that "a biologically effective portion" of the TBX5 gene may be a nucleic acid or a protein and may be a DNA or RNA sequence. It will be further appreciated that such sequences or portions of the gene may contain a region more than about 90%, 91%, 92%, 93%, 94%, 95%, 96%, 97%, 98%, or 99,% or up to 100% similar to the amino acid sequence of the protein encoded by the TBX5 gene and designated SEQ ID NO:12 or may have the same levels of similarity to the TBX5 mRNA designated SEQ ID NO:13, or may have such levels of similarity over a biologically effective region of such sequences that excludes one or more portions thereof that are not necessary for such sequence to achieve the desired biological effect.

In further embodiments such expressing may be achieved in whole or in part by demethylating the DNA sequence in the said colon cancer cells with sequence similarity greater than about 90%, 91%, 92%, 93%, 94%, 95%, 96%, 97%, 98%, 99%, or 100% over at least 15, 20, 25, 30, 35, 40, 45, 50 or more contiguous base pairs to SEQ ID NO:1. It will be understood that demethylating may be achieved in a variety of ways readily understood by those skilled in the art and may be achieved by exposing the cells to reagents such as those set out in the Examples. A range of alternatives will be readily apparent to those skilled in the art.

In alternative embodiments expressing a sequence in colon cancer cells may comprise introducing into the cells an isolated DNA molecule comprising a TBX5 coding sequence (SEQ ID NO:13) operatively linked to a promoter, or comprised in a suitable expression vector, or exposing the cells to the compositions of the other embodiments disclosed herein. In embodiments the colon cancer cells may be cells of a human subject or patient and may be in the body of said subject or patient. A range of promoters and vectors suitable to drive expression of the TBX sequences in mammalian, human, and colorectal cells will be readily identified and implemented by those skilled in the art. The expressed sequence may comprise sequences disclosed in other embodiments and may comprise a region with more than about 90%, 91%, 92%, 93%, 94%, 95%, 96%, 97%, 98%, or 99,% or up to 100% similarity to a portion of the sequence of the TBX5 gene presented as SEQ ID NO:13 or may encode a protein identical or having the same levels of similarity to the TBX5 protein encoded by such nucleic acid sequences and presented as SEQ ID NO:12. In embodiments the introduced TBX5 DNA may be a complete TBX5 gene including a demethylated copy of its endogenous promoter. In an embodiment illustrated in FIG. 2, exogenous expression of TBX5 may be achieved by transfection of target cells with pcDNA3.1-TBX5.

In a further alternative embodiments there is disclosed an isolated nucleic acid molecule comprising a sequence with at least 95% sequence similarity over at least 15 contiguous base pairs to SEQ ID NO:1. In embodiments the isolated nucleic acid molecule may further comprise a suitable vector, which may be a plasmid or a virus, and may comprise added primer sequences or tags. In embodiments the isolated nucleic acid sequence may be demethylated. It will be apparent that further embodiments may comprise sequences that are more or less similar, for example more than about 90%, 91%, 92%, 93%, 94%, 95%, 96%, 97%, 98%, 99% or 100% similar, or may display such similarity over longer or shorter sequences such as about, or more than about 15, 20, 25, 30, 35, 40, 45 and 50 base pairs, as set out in alternative embodiments and in the definitions.

In further alternative embodiments there is disclosed a method for detecting colon cancer in a biological sample, the method comprising the steps of amplifying a region of the DNA in the sample with at least 95% similarity over at least 15 contiguous base pairs to a portion of SEQ ID NO:1; cleaving the amplified DNA with a reagent that preferentially cleaves unmethylated DNA; and comparing the cleavage products to the cleavage products of the isolated DNA molecule to thereby detect colon cancer in the sample. In embodiments the level of sequence similarity to SEQ ID NO:1, and the length of the region of similarity may vary as in the other embodiments.

In embodiments there are disclosed primers for detecting DNA sequences at least 95% similar over 15 or more bases with SEQ ID NO:1.

In embodiments, the materials and methods disclosed may be applied to assess the presence or prognosis of a cancer or other factors relating to the cancer. All of which will be readily understood by those skilled in the art.

EXAMPLES

The following are examples that illustrate materials, methods, and procedures for practicing the subject matter of the embodiments disclosed. It should be understood that the examples and embodiments described herein are for illustrative purposes only and that various modifications or changes in light thereof will be suggested to persons skilled in the art and are to be included within the spirit and purview of this application.

Materials and Methods

Tumor Cell Lines

Eight colon cancer cell lines (DLD-1, HT-29, LOVO, SW480, SW620, CaCO2, LS180, CL14) were obtained from obtained from the American Type Culture Collection (Manassas, Va.). They were cultured in RPMI 1640 medium (Gibco BRL, Rockville, Md.) supplemented with 10%-20% fetal bovine serum (Gibco BRL) and incubated in 5% $CO_2$ at 37° C. Culture media were renewed every two or three days.

Primary Tumor and Normal Tissue Samples

A total of 80 colorectal cancers were obtained at the time of operation. This included 49 males and 31 females. The median age of patients was 69 years (range, 36-91 years). Tumor was staged according to the TNM staging system. Twenty of their corresponding adjacent non-cancerous tissues, which were at least 5 cm away from the tumor edge, were obtained from colon cancer patients at the time of surgery. In addition, 15 age- and gender-matched normal colon mucosae from healthy subjects were collected as normal control. The specimens were snap-frozen in liquid nitrogen and stored at −80° C. for molecular analyses. All subjects were given informed consent for obtaining the study materials. The study protocol was approved by the Clinical Research Ethics Committee of the Chinese University of Hong Kong.

RNA Extraction, Semi-Quantitative RT-PCR and Real-Time PCR Analyses

Total RNA was extracted from cell pellets and tissues using TRIzol Reagent according to the manufacturer's instruction (Molecular Research Center, Inc., Cincinnati, Ohio). cDNA was synthesized from 2 µg total RNA using Transcriptor Reverse Transcriptase (Roche Applied Sciences, Indianapolis, Ind.). For semi-quantitative RT-PCR, a 151 bp fragment of the TBX5 gene was amplified for 36 cycles using AmpliTaq Gold DNA polymerase (Applied Biosystems, Foster City, Calif.) as previously reported (Yu et al, Gastro), with β-actin as internal control. The primer sequences of TBX5 are: forward 5'-CTCAAGCTCACCAACAACCA-3' (SEQ ID NO:2) and reverse 5'-CAGGAAAGACGTGAGTGCAG-3' (SEQ ID NO:3). Real-time PCR was performed using SYBR Green master mixture on HT7900 system according to the manufactures' instructions (Applied Biosystems).

DNA Extraction and Sodium Bisulfite Modification

Genomic DNA was extracted from colon cancer cell lines and colon tissues using the QIAamp DNA Mini kit (Qiagen, Hilden, Germany) and treated with sodium bisulfite using a Zymo DNA Modification kit (Zymo Research, Hornby, Canada). Sodium bisulfite leads to deamination of unmethylated cytosines to uracils without modifying methylated sites. This allows their differentiation by restriction digestion or sequencing.

Combined Bisulfite Restriction Analysis (COBRA)

The methylation level of the promoter region of TBX5 gene was determined by COBRA, a semi-quantitative methylation assay. Hot start PCR amplification with 1.5 µl of bisulfite-treated DNA gives a PCR product of 298 bp, spanning promoter region −902 bp to −603 bp relative to the transcription start site (TSS) of TBX5 transcript variant 1. The primer sequences are forward 5'TATTGTAGTTTGGT-TGAGAGAAAGGA-3' (SEQ ID NO:4) and reverse 5'-CTAAATCTAAACTTACCCCCAACTTC-3' (SEQ ID NO:5). This region contained 19 CpG dinucleotides and 3 BstUI restriction sites (FIG. 1A). PCR products were digested with BstUI (New England Biolabs, Ipswich, Mass.) at 60° C. overnight (New England BioLabs). BstUI cleaved the sequence 5'-CGCG-3' (SEQ ID NO:6) which was partial in the bisulfite-treated methylated DNA, but not the unmethylated DNA. The DNA digests were separated in 10% nondenaturing polyacrylamide gels and stained with ethidium bromide.

Cloned Bisulfite Genomic Sequencing

Cloned bisulfite sequencing was performed to identify the methylation status of 19 CG dinucleotide sites (FIG. 1A). The above PCR products for COBRA from three colon cell-lines, one colon tumor and its adjacent non-cancer tissue and two normal colon tissues were cloned into pCR2.1-TOPO vector (Invitrogen, Carsbad, Calif.). Ten colonies were chosen randomly for plasmid DNA extraction with Qiaprep Spin Mini kit (Qiagen, Valencia, Calif.), and were sequenced. Sequencing analysis was performed by SeqScape software (Applied Biosystems, Foster City, Calif.).

Demethylation with 5-aza-2'-deoxycytidine (5-Aza)

Cells were seeded at a density of $1 \times 10^6$ cells/mL. After 24 hours, cells were treated with 2 µM of the DNA demethylating agent 5-Aza (Sigma-Aldrich, St Louis, Mo.) for 5 days. 5-Aza was replenished every day. Controlled cells were treated with an equivalent concentration of vehicle (DMSO). Cells were then harvested for DNA and RNA extractions.

DNA Mutation Analysis

Genetic deletion and mutation analyses of TBX5 coding exons were performed by DNA direct sequencing. PCR products were purified and sequenced according to the recommendation of the BigDye Terminator v3.1 Cycle Sequencing Kit (Applied Biosystems). Sequence homologies were analyzed using BLAST program of the National Centre for Biological Information (NCBI).

Construction of TBX5 Expression Vector

Mammalian expression vector pcDNA3.1-TBX5 encoding the full-length open reading frame of human TBX5 gene was constructed. Briefly, RNA from human tissue (Ambion, Austin, Tex.) was transcribed into cDNA. Sequence corresponding to the open reading frame clone of TBX5 was amplified and verified by DNA sequencing. PCR amplified inserts were subcloned into the pcDNA3.1 TOPO TA expression vector (Invitrogen). Plasmids used for transfection were isolated using EndoFree Plasmid Maxi Kit (Qiagen).

Western Blot Analysis

Total protein was extracted and protein concentration was measured by the DC protein assay method of Bradford (Bio-Rad, Hercules, Calif.). Thirty micrograms of protein from each sample were used for Western blotting. Bands were quantified by scanning densitometry.

Cell Viability Assay

Cell viability was determined by [3-(4,5-dimethylthiazol-2-yl)-5-(3-carboxymethoxyphenyl)-2-(4-sulfophenyl)-2H-tetrazolium (MTS) assay (Promega, Madison, Wis.). Briefly, cells ($4.5 \times 10^3$/well) were seeded in 96-well plates and TBX5-expressing vector (pcDNA3.1-TBX5) or empty vector (pcDNA3.1) or green fluorescent protein (GFP) plasmid (1.6 µg/each). The transient transfection efficiency was estimated by GFP under a fluorescence microscope. After 48 hr of transfection, 20 µl of reaction solution was added to cultured cells in 100 µl culture medium and incubated at 37° C. for 1.5 h. The optical density was measured at a wavelength of 490 nm using a VICTOR³™ multilabel counter (Perkin Elmer, Fremont, Calif.).

Colony Formation Assay

Cells ($2 \times 10^5$/well) were plated in a 12-well plate and transfected with pcDNA3.1-TBX5, empty vector or GFP plasmid using Lipofectamine™ 2000 (Invitrogen). After 48 h of transfection, cells were collected and plated in a six well plate and selected with 0.6 mg/mL of G418 (Calbiochem, Darmstadt, Germany) for 10 to 14 days, and then with 0.15 mg/mL of G418 for an additional 1 week to establish stable clones. Surviving colonies (≥50 cells/colony) were counted after fixed with methanol/acetone (1:1) and stained with 5% Gentian Violet (ICM Pharma, Singapore) (Yu J, et al., Methylation of protocadherin 10, a novel tumor suppressor, is associated with poor prognosis in patients with gastric cancer. Gastroenterology. 2009; 136:640-51; Yu J, et al., Promoter methylation of the Wnt/beta-catenin signaling antagonist Dkk-3 is associated with poor survival in gastric cancer. Cancer. 2009; 115:49-60). All the experiments were performed in triplicate wells in three independent experiments.

Annexin V Apoptosis Assay

Apoptosis was determined by dual staining with Annexin V:FITC and propidium iodide (Invitrogen, Carlsbad, Calif.). Briefly, pcDNA3.1-TBX5 or empty vector transfected cells ($5 \times 10^5$ cells/well) were harvested at 48 hours post-transfection. Annexin V:FITC and propidium iodide (PI) were added to the cellular suspension according to the manufacturer's instructions, and sample fluorescence of 10,000 cells was analyzed using FACSCalibur System (Becton Dickinson Pharmingen, San Jose, Calif.). The relative proportion of Annexin V-positive cells was determined using the ModFitLT software (Becton Dickinson, San Diego, Calif.) and counted as apoptotic cells. All the experiments were performed three times independently.

Wound-Healing Assay

Cell migration was assessed using a scratch wound assay. Briefly, pcDNA3.1-TBX5 or empty vector stably transfected SW620 cells were cultured in six-well plates ($5 \times 10^5$ cells/well). When the cells grew up to 90% confluence, a single wound was made in the center of cell monolayer using a P-200 pipette tip. At 0, 48, 96 hr of incubation, the wound closure areas were visualized under phase-contrast microscope with a magnification ×100, and the migrated cells were counted. The experiments were performed in triplicate.

Statistical Analysis

Data were expressed as mean±standard deviation (SD). Non-parametric data between two groups was computed by Chi-square test or Fisher Exact test. Multiple group comparisons were made by one-way ANOVA after Bonferroni's correction or Krusal-Wallis test where appropriate. The difference for two different groups was determined by Mann-Whitney U test. The Fisher's Exact Test was used for comparison of patient characteristics by methylation status, and distributions of methylation and covariates by vital status. Patients' age (at entry of follow-up) by vital status was compared using t-test. Relative risks (RRs) of death associated with TBX5 methylation and other predictor variables were estimated from univariate Cox proportional hazards model first. Multivariate Cox models were also constructed to estimate the RR for TBX5 methylation. Overall survival in relation to methylation status was evaluated by Kaplan-Meier survival curve and log-rank test. All analyses were performed using SAS for Windows, version 9, software (SAS Institute, Inc., Cary, N.C.). P-value <0.05 was taken as statistical significance.

Results

Identification of TBX5 as a Novel Gene Down-Regulated or Silenced in Colon Cancer Cells To identify candidate cancer genes with promoter methylation, we performed methylation sensitive arbitrary primed PCR. A preferentially methylated CpG island of TBX5 promoter was identified that epigenetically silences TBX5 expression in human cancer. We then examined the mRNA expression of TBX5 in 8 colon cancer cell lines. RT-PCR showed that TBX5 transcript was silenced or reduced in 7 (88%) cell lines except L5180 (FIG. 1B). In contrast, TBX5 expression was readily detected in normal colon tissues (FIG. 1B), suggesting an aberrant gene silencing of TBX5 in colon cancers.

Promoter Methylation of TBX5 was Correlated with Transcriptional Silencing

To elucidate whether silencing of TBX5 is due to the epigenetic inactivation, TBX5 methylation status was examined by COBRA. Seven cell lines with decreased or silenced TBX5 expression displayed methylated promoter including DLD-1, HT-29, LOVO, SW480, SW620, CaCO2 and CL14, whilst, no methylation was detected in the normal colon tissues (FIG. 1B). We further validated the COBRA results by cloned bisulfite genomic sequencing (BGS) (FIG. 1C). The BGS results were consistent with those of COBRA in which dense methylation was found in methylated cell lines (SW620, HT-29), but not in unmethylated cell line (L5180) and normal colon tissues (FIG. 1C).

Demethylation Treatment with 5-Aza Restored TBX5 Expression

To further reveal whether methylation directly mediates TBX5 silencing, we randomly treated 4 methylated cell lines which showed silence or downregulation of TBX5 with 5-Aza. This treatment resulted in the restoration of TBX5 expression in all cell lines examined (FIG. 1D), inferring promoter methylation directly contributed to the TBX5 silencing.

Genetic Deletion and Mutation of TBX5 were not Detected in Colon Cancer Cell Lines Further genetic deletion and mutation analyses of TBX5 coding exons by DNA direct sequencing did not show any homozygous deletion or mutation in 8 colon cancer cell lines and 20 primary colon cancers, suggesting genetic alteration does not contribute to the silence or downregulation of TBX5 gene in colon cancer.

Ectopic Expression of TBX5 Suppressed Colon Cancer Cell Growth

The frequent silencing of TBX5 mediated by promoter methylation in colon cancer cells but not in normal colon tissue implicated that TBX5 may play a role in tumor growth. To test this speculation, we examined the growth inhibitory effect through ectopic expression of TBX5 in SW620 and CaCO2 which showed no TBX5 expression. Re-expression of TBX5 in the transient transfected SW620 and CaCO2 was confirmed by RT-PCR (FIG. 2A1 and A2), which caused a significant decrease in cell viability in both SW620 ($P<0.05$) and CaCO2 ($P<0.05$) (FIG. 2A3). The suppressive effect on cancer cell proliferation was further confirmed by colony formation assay. A significant reduction of colony numbers was observed in cells stably transfected with pcDNA3.1-TBX5, compared to empty vector in monolayer culture (down to 54-65% of vector controls, $P<0.001$) (FIG. 2B). Thus, TBX5 exhibits growth inhibitory ability in tumor cells and functions as a potential tumor suppressor.

TBX5 Induced Apoptosis

We examined the contribution of apoptosis to the observed growth inhibition of TBX5-transfected cells. Apoptosis was investigated using two-color fluorescence-activated cell sorting analysis. Our results indicated an increase in the numbers of both early apoptotic cells ($12.33\pm0.70\%$ vs. $9.97\pm1.02\%$, $P<0.05$) and late apoptotic cells ($16.2\pm1.48\%$ vs. $10.9\pm0.95\%$, $P<0.01$) in TBX5-transfected SW620 cells than those vector-transfected SW620 cells (FIGS. 3A1 and 3A2). Induction of apoptosis was further confirmed by analysis the expression of apoptosis-related proteins. As shown in FIG. 3A3, re-expression of TBX5 enhanced the protein level of the active form of caspase-3, caspase-7 and nuclear enzyme poly (ADP-ribose) polymerase (PARP) in the stably transfected SW620 cells.

TBX5 Reduced the Migration Rates of SW620 Cells

We tested TBX5 for another tumor-suppressor activity, namely the ability to inhibit cell migration by wound healing assay. As shown in FIG. 3B, a decrease of the cell migration ability in wound closure was observed in SW620 cells transfected with TBX5 as compared to cells transfected with empty vector, as measured after 48 and 96 hr of wound healing, indicating the migration of SW620 cells was inhibited by TBX5.

Frequent TBX5 Methylation in Primary Colon Cancers

We next examined the TBX5 methylation status in 80 primary colon cancers, 20 their adjacent non-tumor tissues and 15 normal colon tissues. Frequent methylation was detected in primary colon cancers (52/80, 65%), but less in paired non-tumor tissues (6/20, 30%) (FIG. 4A1) ($P=0.005$). Further detailed BGS methylation analysis showed densely methylated promoter alleles in tumor, which are rare in paired non-tumor tissue (FIG. 4A2). Fifteen normal colon tissues showed no methylation, indicating that TBX5 methylation was tumor-specific.

TBX5 Methylation was Associated with Poor Survival of Colon Cancer Patients

The association of TBX5 methylation status and clinicopathologic characteristics including clinical outcome was analyzed in 80 colon cancer patients with known survival data (median survival time is 54.4 months, range from 2.3 to 65.6 months). There was no correlation between TBX5 methylation and clinicopathologic features of colon cancer patients such as age, gender, tumor staging, lymph node metastasis, distant metastasis and overall TNM staging. This is shown in Table 1.

TABLE 1

Clinicopathologic features of TBX5 methylation in colon cancer

| Variable | Methylated (n = 52) | % | Non-methylated (n = 28) | % | P value |
|---|---|---|---|---|---|
| Age | | | | | |
| Mean ± SD | 68.6 ± 12.0 | | 66.0 ± 11.6 | | .347 |
| Gender | | | | | |
| M | 31 | 63.3 | 18 | 36.7 | .811 |
| F | 21 | 67.7 | 10 | 32.3 | |
| Tumor staging | | | | | |
| T1 | 1 | 33.3 | 2 | 66.7 | .057 |
| T2 | 1 | 50.0 | 1 | 50.0 | |
| T3 | 42 | 62.7 | 25 | 37.3 | |
| T4 | 8 | 8.0 | 0 | 0.0 | |
| Lymph node | | | | | |
| Negative | 22 | 62.9 | 13 | 37.1 | .815 |
| Positive | 30 | 66.7 | 15 | 33.3 | |
| Metastasis | | | | | |
| No | 36 | 60.0 | 24 | 40.0 | .175 |
| Yes | 16 | 80.0 | 4 | 20.0 | |
| TNM stage | | | | | |
| I | 1 | 33.3 | 2 | 66.7 | .252 |
| II | 18 | 64.3 | 10 | 35.7 | |
| III | 17 | 58.6 | 12 | 41.4 | |
| IV | 16 | 80.0 | 4 | 20.0 | |

An analysis of characteristics of colon cancer patients related to the survival status showed that TBX5 was significantly associated with death. This is shown in Table 2:

TABLE 2

TBX5 methylation relative to survival status

| TBX5 methylation | Alive (n = 43) | % | Dead (n = 37) | % | P value |
|---|---|---|---|---|---|
| Yes | 20 | 38.5 | 32 | 61.5 | .0003 |
| No | 23 | 82.1 | 5 | 17.9 | |

In univariate Cox regression analysis, TBX5 methylation was associated with a significantly increased risk of cancer-related death (RR, 6.21; 95% CI, 2.39-16.2; P=0.0002). After the adjustment for potential confounding factors (TNM staging), multivariate Cox regression analysis showed that TBX5 methylation was a predictor of poorer survival of colon cancer patients (RR, 5.42; 95% CI, 2.06-14.4; P=0.0007). As shown in the Kaplan-Meier survival curves, colon cancer patients with TBX5 methylation had significantly shorter survival than others (P<0.001, log-rank test) (FIG. 4B).

Table 3—Listing of Sequences referred to in this disclosure:

A) SEQ ID NO:1) Sequence of promoter region of the human TBX 5 gene (−902 to −605 bp from the transcription start site) UCSC database: chr12:114,846,852-114,847,149 cactgcagcctggctgagagaaaggacgcgggttgtgctctctggaagc
aaaggggtctgcggcccagctggcctgggagcttgtggccggcgctgga
agctgcccgctctccccgcgggcctgaccttggctcccgccgcagctct
gccggccgactgcctccctgcacatttgctgccgttccagtccttaca
ggaccgggcctggagccaggccatgcttcggaaagccctgggggttggg
gacgcgcaaaacccagaatcgaaccccgaagctgggggcaagtccagat
tcag B) (SEQ ID NO:7) 151 bp amplified portion of human TBX5 transcript variant No. 1 ctcaagctcaccaacaaccacctggacccatttgggcatattattctaa
attccatgcacaaataccagcctagattacacatcgtgaaagcggatga
aaataatggatttggctcaaaaaatacagcgttctgcactcacgtctttcctg C) (SEQ ID NO:12) Human TBX5 amino acid sequence, NCBI accession number: NP 000183

MADADEGFGLAHTPLEPDAKDLPCDSKPESALGAPSKSPSSPQAAFTQQ
GMEGIKVFLHERELWLKFHEVGTEMIITKAGRRMFPSYKVKVTGLNPKT
KYILLMDIVPADDHRYKFADNKWSVTGKAEPAMPGRLYVHPDSPATGAH
WMRQLVSFQKLKLTNNHLDPFGHIILNSMHKYQPRLHIVKADENNGFGS
KNTAFCTHVFPETAFIAVTSYQNHKITQLKIENNPFAKGFRGSDDMELH
RMSRMQSKEYPVVPRSTVRQKVASNHSPFSSESRALSTSSNLGSQYQCE
NGVSGPSQDLLPPPNPYPLPQEHSQIYHCTKRKEEECSTTDHPYKKPYM
ETSPSEEDSFYRSSYPQQQGLGASYRTESAQRQACMYASSAPPSEPVPS
LEDISCNTWPSMPSYSSCTVTTVQPMDRLPYQHFSAHFTSGPLVPRLAG
MANHGSPQLGEGMFQHQTSVAHQPVVRQCGPQTGLQSPGTLQPPEFLYS
HGVPRTLSPHQYHSVHGVGMVPEWSDNS

D) Primer pair for the human TBX5 mRNA:

```
                                          (SEQ ID NO: 2)
         Forward primer 5'-CTCAAGCTCACCAACAACCA-3'

(SEQ ID NO: 3)
         Reverse primer 5'-CAGGAAAGACGTGAGTGCAG-3'.
```

E) Primer pair for the human TBX5 promoter:

```
                                          (SEQ ID NO: 4)
Forward primer 5'TATTGTAGTTTGGTTGAGAGAAAGGA-3'

(SEQ ID NO: 5)
Reverse primer 5'-CTAAATCTAAACTTACCCCCAACTTC-3'.
```

F) BstUI cleavage sequence 5'-CGCG-3' (SEQ ID NO:6)
G) Primers for amplification of the Human TBX5 promoter.

(SEQ ID NO: 8)
Sense primer 5'-GGGTTGTGTTTTTTGGAAGTAAA-3'

(SEQ ID NO: 9)
Sense primer 5'-GTTTAGTTGGTTTGGGAGTTTGT-3'

(SEQ ID NO: 10)
Sense primer 5'-GATTGTTTTTTTGTATATTTTGTTGT-3'

(SEQ ID NO: 11)
Antisense primer 5'-ACAACAAAATATACAAAAAAACAATC-3'

H) (SEQ ID NO:13): *Homo sapiens* T-box 5 (TBX5), transcript variant 1, mRNA sequence UCSC database: chr12: 114791736-114846247

```
catgccttatgcaagagacctcagtcccccggaacaactcgatttccttccaatagaggtctgaggtggactccc
acctcccttcgtgaagagttccctcctctcccccttcctaagaaagtcgatcttggctctatttgtgtcttatgttcatca
ccctcattcctccggagaaagccgggttggtttatgtctttatttattcccggggccaagacgtccggaacctgtgg
ctgcgcagacccggcactgataggcgaagacggagagaaatttacctcccgccgctgcccccagccaaac
gtgacagcgcgcgggccggttgcgtgactcgtgacgtctccaagtcctataggtgcagcggctggtgagatagt
cgctatcgcctggttgcctctttatttactggggtatgcctggtaataaacagtaatatttaatttgtcggagaccaca
aaccaaccttgagctgggaggtacgtgctcttcttgacagacgttggaagaagacctggcctaaagaggtctctt
ttggtggtccttttcaaagtcttcacctgagccctgctctccagcgaggcgcactcctggcttttgcgctccaaagaa
gaggtgggatagttggagagcagaaccttgcgcgggcacagggccctgggcgcaccatggccgacgcaga
cgagggctttggcctggcgcacacgcctctggagcctgacgcaaaagacctgccctgcgattcgaaacccga
gagcgcgctcggggcccccagcaagtcccgtcgtccccgcaggccgccttcacccagcagggcatggagg
gaatcaaagtgtttctccatgaaagagaactgtggctaaaattccacgaagtgggcacggaaatgatcataacc
aaggctggaaggcggatgtttcccagttacaaagtgaaggtgacgggccttaatcccaaaacgaagtacattct
tctcatggacattgtacctgccgacgatcacagatacaaattcgcagataataaatggtctgtgacgggcaaag
ctgagcccgccatgcctggccgcctgtacgtgcacccagactcccccgccaccggggcgcattggatgaggc
agctcgtctccttccagaaactcaagctcaccaacaaccacctggacccatttgggcatattattctaaattccatg
cacaaataccagcctagattacacatcgtgaaagcggatgaaaataatggatttggctcaaaaaatacagcgtt
ctgcactcacgtctttcctgagactgcgtttatagcagtgacttcctaccagaaccacaagatcacgcaattaaag
attgagaataatcccttgccaaaggatttcggggcagtgatgacatggagctgcacagaatgtcaagaatgca
aagtaaagaatatcccgtggtccccaggagcaccgtgaggcaaaaagtggcctccaaccacagtcctttcag
cagcgagtctcgagctctctccacctcatccaatttggggtcccaataccagtgtgagaatggtgtttccggcccct
cccaggacctcctgcctccacccaacccataccactgccccaggagcatagccaaatttaccattgtaccaa
gaggaaagaggaagaatgttccaccacagaccatccctataagaagccctacatggagacatcacccagtg
aagaagattccttctaccgctctagctatccacagcagcagggcctgggtgcctcctacaggacagagtcggca
cagcggcaagctgcatgtatgccagctctgcgcccccagcgagcctgtgcccagcctagaggacatcagct
gcaacacgtggccaagcatgccttcctacagcagctgcaccgtcaccaccgtgcagcccatggacaggctac
cctaccagcacttctccgctcacttcacctcggggcccctggtccctcggctggctggcatggccaaccatggctc
cccacagctgggagagggaatgttccagcaccagacctccgtggcccaccagcctgtggtcaggcagtgtgg
gcctcagactggcctgcagtcccctggcacccttcagcccctgagttcctctactctcatggcgtgccaaggact
ctatcccctcatcagtaccactctgtgcacggagttggcatggtgccagagtggagcgacaatagctaaagtga
ggcctgcttcacaacagacatttcctagagaaagagagagagagaggagaaagagagagaaggagagag
acagtagccaagagaaccccacggacaagattttttcatttcacccaatgttcacatctgcactcaaggtcgctgg
atgctgatctaatcagtagcttgaaaccacaattttaaaaatgtgactttcttgttttgtctcaaaacttaaaaaaaca
aacacaaaaagatgagtcccacccccccactaccaccacacccatcaaccagccacattcacgctactcccca
```

-continued

```
gatctcttcccccattccttcttttgggctctagaaagtcttgcctcattgagtgttttccctagtgcgtagttggagtctg
tccctgtcttggtgttaatgttgacattgttatataataaatgataatatattttttctttcaattttcttaatgggacccagt
cccttatttgggggaggtctgaggcaagtatatttcaaaatatgtacttgcgggattcccttcaagtaaaccatcc
ctgaaacctaaattcacgtttcccccttgactaagaaaagcacctacctctgccatgtgatgtttctgaaaagcctct
gtatgtccccatttgctttggttttgtcctgccttctccaatatcacgtgctcagttttgcctctacttacccatggagtcag
gataacactgacgctccctggcatcctatcttattcagccctaccatcttgccagctctgtcttttccagctgtctgtcgc
taaaacgtggcctatagcttcccttccggaaagcttgctttgaaaaacttaaaaagccccgtttacatgtaggca
ggactgtgataacagtgcaagctctgtgttgacaagagttgtggacaaaaagccaaaataaatattcttcctgatt
aaaaaaattttttttgaaaaaaacaaggccagccccaaccttccaaacctccatcaccaacaacccaaactgg
atgtcaagcaaaatgcacaattcctacagaagaggcaagacacagtcaccaatgatatctcgccaaagaaac
cacgcccacaccaatgccaacacaaaactgtgtttactgaaagccgaaaacagtattaaaaaaagtgtgtaa
gtaaagtgttatggtagggttcttcagatgtaatatttactggtactatttatttataaataggaattctaattaagtaat
aacatgaaatgaaacccagcataggagctggccaagagcttttaattttattgatactcaaaaccaagtttgtgtttt
tttgttttttttttgttttttttcctctttcgaatgtgctttgcttttttgattaaaaagaattttttttttccttttttataaacagaccta
ataaagagaacagggtaagatgtgaggctgagtgtgtttaagtacgtgagagagtgtgagtgtgtttgtaagtga
gtgtccctatgcgattatgtctctttacgttgctaagggggagggtgaggattaagtactcgtgccttatatttgtgtg
ccaattaatgcctaataaataccatgtgcttaaacaagtaaaaaaaaaaaaaaaaaaaaaaaaaaaaaaa
aaaaaaaaaaaaaaaaaaaaaaaaaaaaaaaaaaaaaaaaaaaaaaaaaaaaaaaaaa
```

I) Alternative primer pairs for human TBX5 mRNA sequences

```
Primer pair (i)
Sense primer (+254):
                                (SEQ ID NO: 14)
5'-TAGGCGAAGACGGAGAGAAA-3'

Anti-sense primer (+472):
                                (SEQ ID NO: 15)
5'-GCTCAAGGTTGGTTTGTGGT-3'

Primer pair (ii)
Sense primer (+453):
                                (SEQ ID NO: 16)
5'-ACCACAAACCAACCTTGAGC-3'

Anti-sense primer (+642):
                                (SEQ ID NO: 17)
5'-GCAAGGTTCTGCTCTCCAAC-3'

Primer pair (iii)
Sense primer (+891):
                                (SEQ ID NO: 18)
5'-TCATAACCAAGGCTGGAAGG-3'

Anti-sense primer (+1024):
                                (SEQ ID NO: 19)
5'-GCCCGTCACAGACCATTTAT-3'

Primer pair (iv)
Sense primer (+1504:
                                (SEQ ID NO: 20)
5'-AGCTCTCTCCACCTCATCCA)-3'

Anti-sense primer (+1714):
                                (SEQ ID NO: 21)
5'-TTCACTGGGTGATGTCTCCA-3'

Primer pair (v)
Sense primer (+2494):
                                (SEQ ID NO: 22)
5'-CATCAACCAGCCACATTCAC-3'

Anti-sense primer (+2696):
                                (SEQ ID NO: 23)
5'-AGGGACTGGGTCCCATTAAG-3'

Primer pair (vi
Sense primer (+2863):
                                (SEQ ID NO: 24)
5'-TTTGGTTTTGTCCTGCCTTC-3'

Anti-sense primer (+3019):
                                (SEQ ID NO: 25)
5'-CCACGTTTTAGCGACAGACA-3'

Primer pair (vii
Sense primer (+3317):
                                (SEQ ID NO: 26)
5'-CCAATGCCAACACAAAACTG-3'

Anti-sense primer (+3489):
                                (SEQ ID NO: 27)
5'-AGCTCCTATGCTGGGTTTCA-3'
```

The embodiments and examples presented herein are illustrative of the general nature of the subject matter claimed and are not limiting. It will be understood by those skilled in the art how these embodiments can be readily modified and/or adapted for various applications and in various ways without departing from the spirit and scope of the subject matter disclosed claimed. The claims hereof are to be understood to include without limitation all alternative embodiments and equivalents of the subject matter hereof. Phrases, words and terms employed herein are illustrative and are not limiting. Where permissible by law, all references cited herein are incorporated by reference in their entirety. It will be appreciated that any aspects of the different embodiments disclosed herein may be combined in a range of possible alternative embodiments, and alternative combinations of features, all of which varied combinations of features are to be understood to form a part of the subject matter claimed. Particular embodiments may alternatively comprise or consist of or exclude any one or more of the elements disclosed.

The embodiments of the invention in which an exclusive property or privilege is claimed are defined as follows:

1. A method for assessing risk of colon cancer in a human patient, said method comprising the steps of:
   (1) contacting genomic DNA isolated from a colon mucosa sample from the human patient with a bisulfite, wherein the bisulfite converts unmethylated cytosines in DNA present in the sample to uracils;
   (2) performing a polymerase chain reaction (PCR) to amplify a genomic DNA sequence comprising SEQ ID NO:1 using a primer consisting of SEQ ID NO:4 and a primer consisting of SEQ ID NO:5;
   (3) determining number of methylated cytosine-phosphate-guanine (CpGs) in the genomic sequence amplified in step (2);
   (4) comparing the number of methylated CpGs with the number of methylated CpGs in the genomic sequence from a non-cancer colon mucosa sample and processed through steps (1) to (3); and
   (5) determining the human patient, whose colon mucosa sample contains more methylated CpGs in the genomic sequence determined in step (3) compared to the number of methylated CpGs with the number of methylated CpGs in the genomic sequence from a noncancer colon mucosa tissue sample and processed through steps (1) to (3), as having an increased risk of colon cancer compared with a human subject not diagnosed with colon cancer.

2. The method according to claim 1, wherein the bisulfite is sodium bisulfite.

3. The method according to claim 1, wherein step (2) comprises combined bisulfate restriction analysis (COBRA).

4. The method according to claim 1, wherein step (2) or (3) further comprises using a primer or probe comprising a sequence selected from the group consisting of: SEQ ID NOs:8, 9, 10, and 11.

* * * * *